US012806261B2

(12) United States Patent
Young

(10) Patent No.: US 12,806,261 B2
(45) Date of Patent: Nov. 24, 2026

(54) ROTAVIRUS VACCINES

(71) Applicant: VST LLC, Brookings, SD (US)

(72) Inventor: Alan John Young, Brookings, SD (US)

(73) Assignee: VST LLC, Brookings, SD (US)

( * ) Notice: Subject to any disclaimer, the term of this patent is extended or adjusted under 35 U.S.C. 154(b) by 376 days.

(21) Appl. No.: 18/593,328

(22) Filed: Mar. 1, 2024

(65) Prior Publication Data

US 2025/0276053 A1 Sep. 4, 2025

(51) Int. Cl.

| | |
|---|---|
| ***A61K 39/12*** | (2006.01) |
| ***A61K 39/15*** | (2006.01) |
| ***C07K 14/005*** | (2006.01) |
| ***C07K 14/14*** | (2006.01) |
| *A61K 39/00* | (2006.01) |

(52) U.S. Cl.

CPC ............ *A61K 39/12* (2013.01); *C07K 14/005* (2013.01); *A61K 39/15* (2013.01); *A61K 2039/54* (2013.01); *A61K 2039/541* (2013.01); *A61K 2039/545* (2013.01); *A61K 2039/55566* (2013.01); *A61K 2039/575* (2013.01); *C07K 14/14* (2013.01); *C12N 2720/12322* (2013.01); *C12N 2720/12334* (2013.01); *C12N 2720/12351* (2013.01)

(58) Field of Classification Search

None

See application file for complete search history.

(56) References Cited

PUBLICATIONS

Burnett et al., Paediatr Drugs, Jun. 2018, 20(3): 223-233. (Year: 2018).*

* cited by examiner

*Primary Examiner* — Nicole Kinsey White

(57) ABSTRACT

The present invention describes immunogenic compositions containing immunogenic polypeptides of Rotavirus (RV), including immunogenic compositions containing antigens other than RV antigens and antigens that may be used in immunization against pathogens that cause diarrheal diseases. Methods of eliciting an immune response with the immunogenic compositions as disclosed and methods of treating an RV infection are also described.

11 Claims, 4 Drawing Sheets

Specification includes a Sequence Listing.

ROTAVIRUS VACCINES

BACKGROUND OF THE INVENTION

Field of Invention

The present invention pertains generally to compositions that elicit immune responses against Rotavirus infection. In particular, the invention relates to immunogenic compositions (e.g., vaccines) comprising immunogenic polypeptides of Rotavirus A and C. Immunogenic compositions, in addition, may contain antigens other than Rotavirus antigens. Methods of eliciting an immune response with the immunogenic compositions as disclosed herein and methods of treating a Rotavirus infection are also described.

Background Information

Swine Rotaviruses are a prevalent and economically devastating disease that continue to plague the swine industry. Current vaccines necessarily rely on outdated strains that may not cover the full breadth of Rotaviruses impacting producers today.

Rotaviruses (RVs) are endemic in swine populations, and all swine herds certainly have a history of RV infection and circulation. Rotavirus A (RVA) and C (RVC) are the most common among all RV species reported in swine. RVA was considered most prevalent and pathogenic in swine; however, RVC has been emerging as a significant cause of enteritis in newborn piglets. Newborn piglets are highly susceptible to RV infection at birth.

Rotaviruses (RVs) are double-stranded RNA viruses belonging to the Rotavirus genus in the Reoviridae family. The RV genome is approximately 18,500 bp in size and consists of 11 segments of dsRNA encoding six structural proteins (VP1-VP4, VP6 and VP7) and five non-structural proteins (NSP 1-NSP5/6). The inner capsid of the virion comprises VP1, VP2, and VP3 segments. The VP6 forms the middle layer of the capsid, while the outer capsid is composed of the VP7 and VP4 proteins. VP7, a glycoprotein with a molecular weight of 37 kDa, constitutes 30% of the virus protein, and forms the smooth external surface of the outer shell. The minor component of the outer shell, VP4, is present as a series of spikes that project outward from the VP7 shell. VP4 is non-glycosylated, has a molecular weight of 88 kDa, and constitutes 1.5% of the virus protein. The VP4 gets proteolytically cleaved into VP5* and VP8* segments. The VP8* forms the head of the VP4 protein which helps in host attachment and infectivity. VP4 has been implicated in several important functions, including cell attachment and penetration, hemagglutination, neutralization, host range, and virulence. RVs are unique since the NSP4 produces an enterotoxin, which contributes to viral pathogenesis.

RV species are classified based on sequencing of the VP6 gene. A binary classification system is used to address vast Rotavirus diversity on the basis of sequencing of G (VP7) and P types (VP4). The dual (G/P) tying system has been extended to a complete genome classification system based on nucleotide sequencing of all 11 RV segments with nucleotide percent identity cut-off values set for each segment. In this system, VP7-VP4-VP6-VP1-VP2-VP3-NSP1-NSP2-NSP3-NSP4-NSP5/6 RV genes are designated as Gx-P[x]-Ix-Rx-Cx-Mx-Ax-Nx-Tx-Ex-Hx.

Currently, nine RV species (RVA-RVD and RVF-J) have been classified by the International Committee on Taxonomy of Viruses. However, only species A, B, C, E, and H have been reported from swine. RVs are ubiquitous in nature, and mixed infections involving several RV strains appear more common as pigs grow older. Once infected, piglets may exhibit clinical or subclinical symptoms and eventual recovery in most cases. However, neonatal and suckling piglets without an established adaptive immune system are worst affected. RVA is the most characterized species among RVs due to its wide host range, high prevalence, and pathogenicity.

RV transmission is through fecal-oral route, and the piglets become infected with RV shed from sows and other piglets. The target sites of RV replication are the mature, non-dividing enterocytes in the small intestine. Enterocytes contain the enterokinase enzyme which is necessary for activating trypsin, which activates RVs and facilitates viral entry into the cells. The virus particularly affects the middle and the tip of the villi causing destruction and eventually resulting in villous atrophy. The extent of villous atrophy induced by RV is lesser compared to other enteric viral pathogens of pigs such as transmissible gastroenteritis virus (TGEv) or porcine epidemic diarrhea virus (PEDv). The normal villus-height/crypt-depth ratio of the intestinal villi is approximately 7:1. TGEv reduces this ratio to 1:1, whereas RV infection slightly changes it to 5:1. The severity of RV infection depends on the length of the villi and the percentage of enterocytes that are affected. Eventually, the mature columnar epithelial cells on the villi are replaced by immature cuboidal enterocytes that are unable to produce digestive enzymes and have lost their absorptive capabilities.

RVA has been reported from swine population globally. In the US, RVA infection is most common in pigs 21-55 days old, with slightly less neonatal cases. However, RVA is still a major cause of neonatal diarrhea in piglets worldwide. RVA prevalence ranging from 9.4% to 81.1% have been reported from swine populations in the US. To date, 42 G genotypes and 58 P genotypes have been identified within RVAs. Of these, 12 G genotypes (G1-G6, G8-G12, and G26) and 16 P genotypes (P[1], P[5]-P[8], P [11], P[13]-P[14], P[19], P[23], P[26]-P [27], P[32] and P[34]) have been reported from swine populations. A study reported G5 (71.43%) as the most prevalent RVA genotype in the US followed by G4 (8.19%), G3 (3.57%), G9 (2.31%), G11 (1.89%), G10 (1.26%), and G1 (1.05%). Prevalence of other genotypes (G2, G6, and G10) was less than 1%. Among P genotypes, P[7] was the most common genotype (77.22%) followed by P[6](12.07%), whereas other P types individually constituted less than 1% of the reported RVA genotypes.

RVC has been emerging as a significant cause of enteritis in neonatal piglets. Porcine RVC was first identified in 1980 and considered as an enteric pathogen with a moderate prevalence rate between 4 and 31%. In the US, RVC is a major cause of diarrhea in neonatal pigs, particularly in piglets younger than 3 days old. In the US, 51.1% of porcine intestinal samples collected during 2009-2011 were positive for RVC. A study reported an overall RVC prevalence of 19.5% in diarrheic and non-diarrheic piglets collected from swine farms located in Ohio, US. The prevalence of RVC was 23.5% among nursing piglets compared to only 8.5% in weaned piglets. Another study from the US detected RVC in 46% samples of porcine origin (feces, fecal swabs, intestinal, or lung tissues) collected during 2009-2011 in the US and Canada. Of these, RVC was detected in 16% of samples from very young pigs (<3 days old) and 21% of samples from young pigs (4-20 days old). Interestingly, 34% of RVC positive samples were negative for RVA/RVB, and the highest percentage of single RVC infections was in very young (78%, <3 days) and young pigs (65%, 4-22 days)

compared to 6-39% in older age groups. Interestingly, single infections of RVC are more common in 0-3 days old piglets, with co-infection with other RV species being more prevalent post-weaning.

In swine, 15 G genotypes (G12, G13, G8, G6, G5, G14, G9, G1, G17, G15, G7, G10, G3, G18, G16), and 16 P genotypes (P[1], P[5]-P[9], and P[12]-P[21]) of RVC have been identified. The G6 genotype (70%) was the dominant RVC genotype followed by G5 (17%), G1 (12%), and G9 (1%). A study reported higher fecal prevalence (76.1%) of RVC from healthy and diarrheic piglets in the US. A recent study reported presence of RVC in piglets less than 1-week-old in Australian swine herds. Importantly, single RVC genotypes (either G5 or G6) were detected from neonatal piglets; however, older piglets (5-11 weeks) harbored multiple genotypes of RVC (G1 and G3). It is evident that RVC infections are more prevalent among neonatal piglets than weaned piglets, but the reason(s) are not completely understood. While not being bound by theory, likely reasons include lack of an RVC vaccine for use in swine, insufficient maternal RVC antibodies in colostrum or low minimum infectious dose of RVC required for infecting piglets compared to other swine enteric viruses.

As Rotaviruses exist in multiple genotypes (generally denoted P and G types) due to reassortment of viral genes, a more flexible and temporally responsive vaccine platform is required to match the needs of producers with modern vaccine technology.

SUMMARY OF THE INVENTION

The present invention provides immunogenic compositions comprising Rotavirus antigens, in particular as a part of subunit vaccines.

In embodiments, methods for producing Rotavirus-derived immunogenic polypeptides and/or peptides may be mixed or co-expressed with adjuvants are disclosed. Immunogenic compositions may include one or more polypeptides and/or adjuvants as described herein. For example, immunogenic compositions may comprise other antigens that may be used in immunization against pathogens that cause other diseases, such as antigens derived from non-Rotavirus pathogens.

In embodiments, a process for producing a polypeptide is disclosed including the step of culturing a host cell transformed with a nucleic acid as described herein under conditions which induce polypeptide expression. In a related aspect, a Rotavirus protein may be expressed by recombinant technology and used to develop an immunogenic composition comprising a recombinant antigenic subunit, where such expressed polypeptide is generated using baculovirus/insect cell methodology.

In one aspect, a process for producing nucleic acid is disclosed, where the nucleic acid encoding a Rotavirus derived protein or polypeptide is prepared (at least in part) by chemical synthesis. In a related aspect, the process includes amplifying nucleic acids using a primer-based amplification method (e.g., PCR).

In another aspect, a process for producing a protein complex is disclosed, including administering Rotavirus derived polypeptides, or fragments thereof, to a subject. In a related aspect, the process includes admixing Rotavirus-derived polypeptides with a pharmaceutically acceptable carrier or diluent, including an adjuvant. In a related aspect, the adjuvant is a Water/Oil/Water adjuvant. In a further related aspect, the composition may include the set of polypeptides as set forth in SEQ ID NOs:2 and 46 or SEQ ID NOs:2, 4, 6, 8, 10, 12, 14, 16, and 18.

In embodiments, a method of eliciting an immunological response in a subject is disclosed including administering a composition of the instant disclosure. In a related aspect, the method further includes administering an adjuvant. In a further related aspect, the method includes administering the immunogenic composition to the subject via topical, parenteral or mucosal route.

In one aspect, the administration may be multiple administrations, where a first immunogenic composition and a second immunogenic composition are the same. In another aspect, the first immunogenic composition and the second immunogenic composition are different.

In one aspect, administration is performed two or more times.

In embodiments, a method for treating an infection by a Rotavirus is disclosed including administering to a subject in need thereof a therapeutically effective amount of an immunogenic composition as described herein. In a related aspect, the Rotavirus is of the G5/P[7] genotype for RVA and G6 genotype for RVC. In a further related aspect, the subject is a neonatal piglet.

In one aspect, multiple therapeutically effective doses of the immunogenic composition are administered to a subject.

In a related aspect, the method includes mucosally administering a therapeutically effective amount of a first immunogenic composition comprising the set of Rotavirus antigens and topically or parenterally administering a therapeutically effective amount of a second immunogenic composition comprising the set of Rotavirus antigens.

In one aspect, multiple therapeutically effective doses of the immunogenic composition are administered to a subject. In another aspect, an immunogenic composition comprises a separate, non-Rotavirus antigen.

These and other embodiments of the instant subject matter as disclosed will readily occur to those of skill in the art in view of the instant disclosure.

DETAILED DESCRIPTION OF THE INVENTION

Figure 1A:
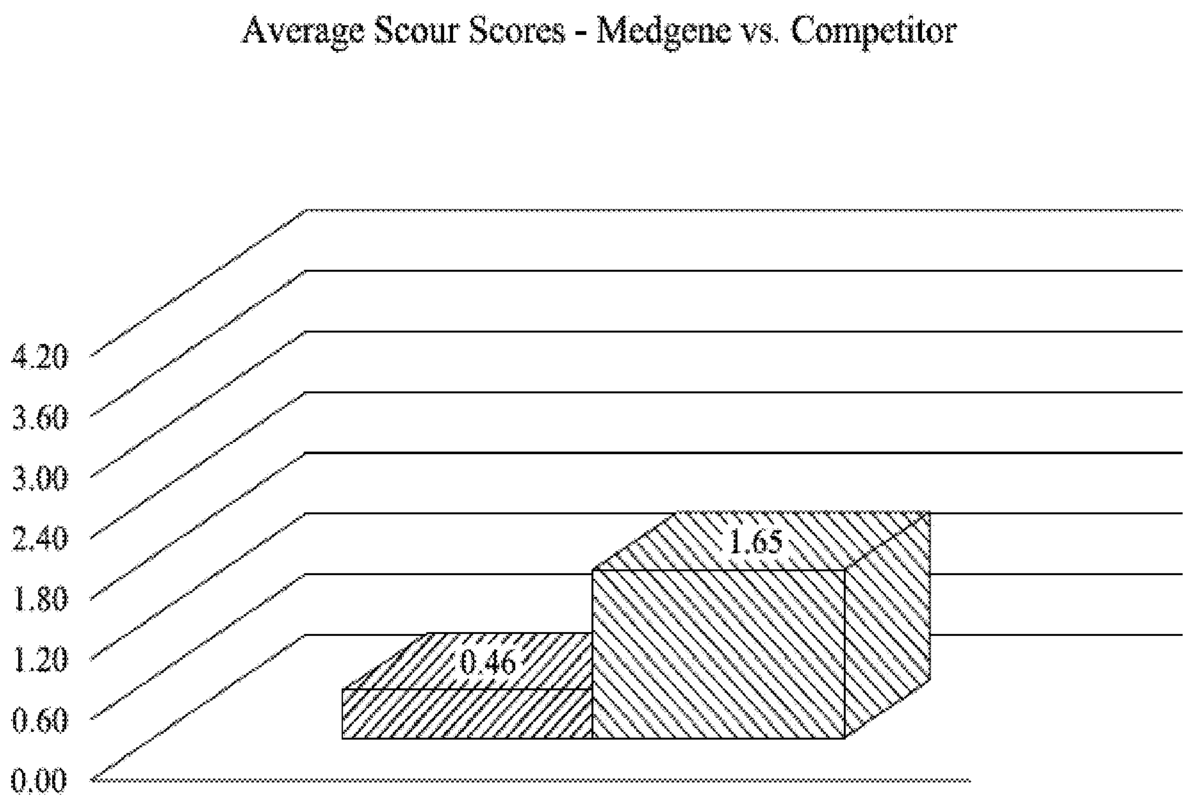
FIGS. 1 *a, b* illustrate the results from the vaccination between MEDGENE™'s (Applicants') vaccine and an RNA-based vaccine in swine.

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a," "an," and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein may be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the art given the context in which it is used, "about" and "approximately" will mean plus or minus <10% of particular term and "substantially" and "significantly" will mean plus or minus >10% of the particular term. In embodiments, compositions may "contain," "comprise" or "consist essentially of" a particular component or group of components, where the skilled artisan would understand the latter to mean the scope of the claim is limited to the specified materials or steps "and those that do not materially affect the basic and novel characteristic(s)" of the claimed invention.

We have shown that a baculovirus-produced, rotavirus specific bivalent vaccine elicited high titers of neutralizing antibodies against the target Rotavirus A. Mice were immunized with several putative subunit vaccines, and blood collected to analyze immunoreactivity. Mice immunized with a bivalent vaccine developed neutralizing titers exceeding 1:640 whereas control mice failed to develop any titers. Interesting, the inclusion of additional protein targets did not increase vaccine effectiveness, and in fact a trivalent vaccine reduced apparent neutralization titers to 1:320. Based upon this encouraging data, we have continued to examine the specificity of the immune response in vaccination trials. Specifically, mice were vaccinated with baculovirus-produced proteins whose sequences were derived from circulating strains of protein Rotavirus. Sera obtained from these vaccinated animals was then used in standard serum neutralization (SN) assays as a correlate of expected protection. While these experiments are ongoing, we have established critical epitopes within the target proteins as evidenced by effective cross-neutralization in vitro, combined with in silico analysis of predicted protein structure. Based upon the data obtained, it is clear that cross-protection against significantly divergent Rotavirus A isolates can be generated, and these predictive algorithms are currently being tested directly in swine. Given new regulatory pathways, this work opens the door to the availability of targeted vaccines to protect against currently circulating strains of Rotavirus A, and the potential for development of vaccines against other strains of Rotaviruses (B and C) that can be easily produced using analogous technology.

As used herein, the terms "Rotavirus" and "Rotavirus-like virus" refer to members of the genus Rotavirus of the family Reoviridae. The term Rotavirus includes strains in all genogroups of the virus. Currently, nine species of Rotavirus referred to as follows: A, B, C, D, E, F, G, H, I, and J. A large number of Rotaviruse isolates have been partially or completely sequenced. The term Rotavirus also includes isolates not characterized at the time of filing.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation and the like. Furthermore, for purposes of the present disclosure, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

"Substantially purified" generally refers to isolation of a substance (compound, polynucleotide, protein, polypeptide, polypeptide composition) such that the substance comprises the majority percent of the sample in which it resides. Typically, in a sample, a substantially purified component comprises about 50%, about 80%-85%, or about 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism or cell with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used include fluorescein, rhodamine, dansyl, umbelliferone, Texas red, luminol, acradimum esters, NADPH and $\alpha$-$\beta$-galactosidase.

"Homology" refers to the percent identity between two polynucleotide or two polypeptide moieties. Two nucleic acid, or two polypeptide sequences are "substantially homologous" to each other when the sequences exhibit at least about 50% sequence identity, at least about 75% sequence identity, at least about 80%-85% sequence identity, at least about 90% sequence identity, and at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity may be determined by a direct comparison of the sequence information between two molecules by aligning the sequences, counting the exact number of matches between the two aligned sequences, dividing by the length of the shorter sequence, and multiplying the result by 100. Readily available computer programs may be used to aid in the analysis, such as ALIGN, Dayhoff, M. O. in Atlas of Protein Sequence and Structure M. O. Dayhoff, ed., 5 Suppl. 3:353-358, National biomedical Research Foundation, Washington, D.C., which adapts the local homology algorithm of Smith and Waterman Advances in Appl. Math.

2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence may be determined using the homology algorithm of Smith and Waterman with a default scoring table and a gap penalty of six nucleotide positions.

Another method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, CA). From this suite of packages the Smith-Waterman algorithm may be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology may be determined by hybridization of polynucleotides under conditions which form stable duplexes between homologous regions, followed by digestion with single-stranded-specific nuclease(s), and size determination of the digested fragments. DNA sequences that are substantially homologous may be identified in a Southern hybridization experiment under, for example, stringent conditions, as defined for that particular system. Defining appropriate hybridization conditions is within the skill of the art.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells," "host cells," "cells," "cell lines," "cell cultures," and other such terms denoting microorganisms or higher eukaryotic cell lines cultured as unicellular entities refer to cells which may be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence may be determined by a start codon at the 5' (amino) terminus and a translation stop codon at the 3' (carboxy) terminus. A coding sequence may include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

The term "nucleic acid" includes DNA and RNA, and also their analogues, such as those containing modified backbones (e.g., phosphorothioates, and the like), and also peptide nucleic acids (PNA), and the like. The present disclosure provides nucleic acids comprising sequences complementary to those described above (e.g., for antisense or probing purposes).

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences may be present between the promoter sequence and the coding sequence and the promoter sequence may still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, at least 8 to 10 amino acids, and at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. In embodiments, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, less than about 70%, and less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. Such techniques may be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which may transfer nucleic acid sequences to target cells. Thus, the term includes cloning and expression vehicles, as well as viral vectors.

By "fragment" is intended a molecule consisting of only a part of the intact full-length sequence and structure. A fragment of a polypeptide may include a C-terminal deletion, an N-terminal deletion, and/or an internal deletion of the native polypeptide. A fragment of a polypeptide will generally include at least about 5-10 contiguous amino acid residues of the full-length molecule, at least about 15-25 contiguous amino acid residues of the full-length molecule, and at least about 20-50 or more contiguous amino acid residues of the full-length molecule, or any integer between 5 amino acids and the number of amino acids in the full-length sequence, provided that the fragment in question retains the ability to elicit the desired biological response. A fragment of a nucleic acid may include a 5'-deletion, a 3'-deletion, and/or an internal deletion of a nucleic acid. Nucleic acid fragments will generally include at least about 5-1000 contiguous nucleotide bases of the full-length molecule and may include at least 5, 10, 15, 20, 25, 30, 40, 50, 60, 75, 100, 150, 250 or at least 500 contiguous nucleotides of the full-length molecule, or any integer between 5 nucleotides and the number of nucleotides in the full-length sequence. Such fragments may be useful in hybridization, amplification, production of immunogenic fragments, or nucleic acid immunization.

By "immunogenic fragment" is meant a fragment of an immunogen which includes one or more epitopes and thus may modulate an immune response or may act as an adjuvant for a co-administered antigen. Such fragments may be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871, incorporated herein by reference in its entirety. Similarly, conformational epitopes are readily identified by determining spatial conformation of amino acids such as by, e.g., x-ray crystallography and 2-dimensional nuclear magnetic resonance.

Immunogenic fragments, for purposes of the present disclosure, will usually be at least about 2 amino acids in length, about 5 amino acids in length, and at least about 10 to about 15 amino acids in length. There is no critical upper limit to the length of the fragment, which could comprise nearly the full-length of the protein sequence, or even a fusion protein comprising two or more epitopes.

As used herein, the term "epitope" generally refers to the site on an antigen which is recognized by a T-cell receptor and/or an antibody. In embodiments, it is a short peptide derived from or as part of a protein antigen. However, the term is also intended to include peptides with glycopeptides and carbohydrate epitopes. Several different epitopes may be carried by a single antigenic molecule. The term "epitope" also includes modified sequences of amino acids or carbohydrates which stimulate responses which recognize the whole organism. It is advantageous if the selected epitope is an epitope of an infectious agent, which agent causes the infectious disease.

The epitope may be generated from knowledge of the amino acid and corresponding DNA sequences of the peptide or polypeptide, as well as from the nature of particular amino acids (e.g., size, charge, and the like) and the codon dictionary, without undue experimentation. Some guidelines in determining whether a protein will stimulate a response, include: Peptide length—the peptide is about 8 or 9 amino acids long to fit into the MHC class I complex and about 13-25 amino acids long to fit into a class II MHC complex. This length is a minimum for the peptide to bind to the MHC complex. In one aspect, the peptides may be longer than these lengths because cells may cut peptides. The peptide may contain an appropriate anchor motif which will enable it to bind to the various class I or class II molecules with high enough specificity to generate an immune response. This may be done, without undue experimentation, by comparing the sequence of the protein of interest with published structures of peptides associated with the MHC molecules. Thus, the skilled artisan may ascertain an epitope of interest by comparing the protein sequence with sequences listed in the protein database.

As used herein, the term "T cell epitope" refers generally to those features of a peptide structure which are capable of inducing a T cell response and a "B cell epitope" refers generally to those features of a peptide structure which are capable of inducing a B cell response.

An "immunological response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes may be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. Recent methods of measuring cell-mediated immune response include measurement of intracellular cytokines or cytokine secretion by T-cell populations, or by measurement of epitope specific T-cells.

Thus, an immunological response as used herein may be one that stimulates the production of antibodies (e.g., neutralizing antibodies that block bacterial toxins and pathogens such as viruses entering cells and replicating by binding to toxins and pathogens, typically protecting cells from infection and destruction). The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses may be determined using standard immunoassays and neutralization assays, well known in the art. The innate immune system of mammals also recognizes and responds to molecular features of pathogenic organisms via activation of Toll-like receptors and similar receptor molecules on immune cells. Upon activation of the innate immune system, various non-adaptive immune response cells are activated to, e.g., produce various cytokines, lymphokines and chemokines. Cells activated by an innate immune response include immature and mature Dendritic cells of the monocyte and plamsacytoid lineage (MDC, PDC), as well as gamma, delta, alpha and beta T cells and B cells and the like. Thus, the present disclosure also contemplates an immune response wherein the immune response involves both an innate and adaptive response.

An "immunogenic composition" is a composition that comprises an antigenic molecule where administration of the composition to a subject results in the development in the subject of a humoral and/or a cellular immune response to the antigenic molecule of interest.

The terms "immunogenic" protein or polypeptide refer to an amino acid sequence which elicits an immunological response as described above. An "immunogenic" protein or polypeptide, as used herein, includes the full-length sequence of the protein in question, including the precursor and mature forms, analogs thereof, or immunogenic fragments thereof.

"Gene transfer" or "gene delivery" refers to methods or systems for reliably inserting DNA or RNA of interest into a host cell. Such methods may result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses. When used for immunization, such gene delivery expression vectors may be referred to as vaccines or vaccine vectors.

The term "derived from" is used herein to identify the original source of a molecule but is not meant to limit the method by which the molecule is made which may be, for example, by chemical synthesis or recombinant means.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

A polynucleotide "derived from" a designated sequence refers to a polynucleotide sequence which comprises a contiguous sequence of approximately at least about 6 nucleotides, at least about 8 nucleotides, at least about 10-12 nucleotides, and at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

A Rotavirus polynucleotide, oligonucleotide, nucleic acid, protein, polypeptide, or peptide, as defined above, is a molecule derived from a Rotavirus, respectively, including, without limitation, any of the various isolates of Rotavirus. The molecule need not be physically derived from the particular isolate in question, but may be synthetically or recombinantly produced.

The Rotavirus genome of consists of eleven segments of ds RNA encoding six structural proteins VP1-VP4, VP6 and VP7 and five non-structural proteins NSP1-NSP5/6.

Nucleic acid and protein sequences for a number of Rotavirus isolates are also known. Representative Rotavirus sequences are presented in SEQ ID NOs:1, 3, 5, 7, 9, 11, 13, 15, 17 and 45. Additional representative sequences, including sequences of Rotavirus, and their encoded polypeptides from Rotavirus isolates are listed in the National Center for Biotechnology Information (NCBI) database. See, for example, but not limited to, GenBank entries: BAA03855.1; BAF80156.1, CAA67568.1, BAF59645.1, X99126.1, AB275386.1, D16352.1 and AB008292.1, all of which sequences (as entered by the date of filing of this application) are herein incorporated by reference.

As used herein, the terms "capsid protein" or "capsid polypeptide" or "outer capsid" in reference to a Rotavirus refer to VP4 or VP7 comprising a sequence homologous or identical to the capsid polypeptide of a Rotavirus VP4 or VP7, and include sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99% or greater, but less than 100% sequence identity thereto.

As used herein, the terms "minor structural protein" or "minor structural polypeptide" or "inner or middle capsid" in reference to a Rotavirus refer to a polypeptide comprising VP1, VP2, VP3, and VP6 sequence homologous or identical to the polypeptide encoded by the open reading frame following the coding region for the capsid protein in the Rotavirus genome, and include sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99% or greater, but less than 100% sequence identity thereto.

An "antigen" refers to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but may be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which may mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules and any functional fragments obtained from such molecules, wherein such fragments retain specific-binding properties of the parent antibody molecule.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. In particular, Rotavirus may be obtained from biological samples including, but not limited to, oral or fecal matter.

By "subject" is meant any member of the family Suidae, genus *sus*, and more specifically, *Sus domesticus*. The term does not denote a particular age. Thus, both adult and newborn individuals are intended to be covered, as well as females.

The terms "variant," "analog" and "mutein" refer to biologically active derivatives of the reference molecule that retain desired activity, such as antigenic activity in inducing an immune response against Rotavirus. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, and the like), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301). In embodiments, the analog or mutein has at least the same antigenic activity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that may tolerate change by reference to Hopp/Woods and Kyte-Doolittle plots, well known in the art.

The term "multiple epitope fusion antigen" or "multiple epitope fusion protein" as used herein intends a polypeptide in which multiple Rotavirus antigens are part of a single, continuous chain of amino acids, which chain does not occur in nature. The Rotavirus antigens may be connected directly to each other by peptide bonds or may be separated by intervening amino acid sequences. The fusion antigens may also contain sequences exogenous to the Rotavirus. Moreover, the sequences present may be from multiple genotypes and/or isolates of Rotavirus.

By "therapeutically effective amount" in the context of the immunogenic compositions is meant an amount of an immunogen (e.g., immunogenic polypeptide, fusion protein, polyprotein, or nucleic acid encoding an antigen) which will induce an immunological response, either for antibody production or for treatment or prevention of Rotavirus infection. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γ, δ-T cell populations.

For purposes of the present disclosure, an "effective amount" of an adjuvant will be that amount which enhances an immunological response to a co-administered antigen or nucleic acid encoding an antigen.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

Before describing the present disclosure in detail, it is to be understood that the practice of the present disclosure will employ, unless otherwise indicated, conventional methods of virology, microbiology, molecular biology, recombinant DNA techniques and immunology all of which are within the ordinary skill of the art. Such techniques are explained fully in the literature. Although a number of methods and materials similar or equivalent to those described herein may be used in the practice of the present invention as claimed, the materials and methods are described herein.

The present disclosure includes compositions and methods for immunizing a subject against Rotavirus infection. The instant disclosure provides immunogenic compositions comprising nucleic acids encoding capsid proteins and/or other immunogenic polypeptides from one or more strains of Rotavirus, compositions comprising immunogenic polypeptides derived from one or more strains of Rotavirus. Immunogenic polypeptides to be used in the practice of the instant subject matter may include Rotavirus-derived polypeptides, including multiple epitope fusion antigens, and/or Rotavirus-encoded polyproteins. In addition, immunogenic compositions may comprise one or more adjuvants or nucleic acids encoding adjuvants, wherein immunogenic polypeptides are mixed or co-expressed with adjuvants. Immunogenic compositions may also comprise additional antigens other than Rotavirus antigens, such as antigens that may be used in immunization against pathogens that cause diarrheal diseases.

In order to further an understanding of the subject matter as disclosed, a more detailed discussion is provided below regarding the production of nucleic acids and polypeptides for use in immunogenic compositions and methods of using such compositions in the treatment or prevention of Rotavirus infection.

Structural Polypeptides, Nonstructural Polypeptides, and Polyproteins

The immunogenic compositions described herein may comprise one or more polypeptides derived from one or more genotypes and/or isolates of Rotavirus. Polypeptides that may be used in the practice of the subject matter as disclosed herein include structural proteins, nonstructural proteins, and polyproteins. Such polypeptides may be full-length proteins or variants or immunogenic fragments thereof capable of eliciting an immune response to a Rotavirus.

The polypeptides in immunogenic compositions may be encoded by any region of a Rotavirus genome. Multiple polypeptides may be included in immunogenic compositions. Such compositions may comprise polypeptides from the same Rotavirus isolate or from different strains and isolates, including isolates having any of the various species of Rotavirus (e.g., Rotavirus A, B, C, D, E, F, G, H, I or J), to provide increased protection against a broad range of Rotavirus species. Multiple viral strains of Rotavirus are known (or not), and multiple polypeptides comprising epitopes derived from any of these strains may be used in immunogenic compositions.

The antigens used in the immunogenic compositions of the present disclosure may be present in the composition as individual separate polypeptides. Generally, the recombinant proteins of the present disclosure are expressed as a GST-fusion protein and/or a His-tagged fusion protein.

Multiepitope Fusion Proteins

The immunogenic compositions described herein may also comprise multiple epitope fusion proteins. Such fusion proteins include multiple epitopes derived from two or more viral polypeptides of one or more genotypes and/or isolates of Rotavirus. Multiple epitope fusion proteins offer two principal advantages: first, a polypeptide that may be unstable or poorly expressed on its own may be assisted by adding a suitable hybrid partner that overcomes the problem; second, commercial manufacture is simplified as only one expression and purification need be employed in order to produce two polypeptides which are both antigenically useful.

Multiepitope fusion proteins may contain one or more of the various domains of Rotavirus full-length proteins VP4 and/or VP7 (also referred to herein as Rotavirus major structural proteins) and/or VP1, Vp2, VP3, and/or VP6 (also referred to herein as a Rotavirus minor structural protein); and NSP1-NSP5/6 (also referred to herein as a Rotavirus non-structural protein), or fragments thereof, derived from one or more Rotavirus isolates. The polypeptides in fusion proteins may be derived from the same Rotavirus isolate or from different strains and isolates, including isolates having any of the various Rotavirus species, to provide increased protection against a broad range of Rotavirus species. Multiple viral strains of Rotavirus are known, and epitopes derived from any of these strains may be used in a fusion protein.

It is well known that any given species of organism varies from one individual organism to another and further that a given organism such as a virus may have a number of different strains. For example, as explained above, Rotavirus includes at least nine species (A-J). Each strain includes a number of antigenic determinants that are in homologous regions present in all species of Rotavirus but are slightly different from one viral strain to another. Thus, a multiple epitope fusion antigen may include multiple polypeptides from different viral strains of Rotavirus, each comprising a particular homologous region but each having a different form of an antigenic determinant. In general, antigenic determinants may have a high degree of homology in terms of amino acid sequence, which degree of homology is generally 30% or more, 40% or more, when aligned.

Multiple epitope fusion antigens may be represented by the formula $NH_2\text{-A-}\{\text{-X-L-}\}_n\text{-B—COOH}$, wherein: X is an amino acid sequence of a Rotavirus antigen or a fragment thereof; L is an optional linker amino acid sequence; A is an optional N-terminal amino acid sequence; B is an optional C-terminal amino acid sequence; and n is 2, 3, 4, 5, 6, 7, 8, 9, 10, 11, 12, 13, 14 or 15.

If an —X— moiety has a leader peptide sequence in its wild-type form, this may be included or omitted in the multiple epitope fusion antigen. In some embodiments, the leader peptides will be deleted except for that of the —X— moiety located at the N-terminus of the hybrid protein i.e., the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of (—X-L-), linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, and the like. Linker amino acid sequence(s)-L- will typically be short, e.g., 20 or fewer amino acids (i.e., 20, 19, 18, 17, 16, 15, 14, 13, 12, 11, 10, 9, 8, 7, 6, 5, 4, 3, 2, 1). Examples include short peptide sequences which facilitate cloning, poly-glycine linkers (Gly, where n=2, 3, 4, 5, 6, 7, 8, 9, 10 or more), and histidine tags ($His_n$ where n=3, 4, 5, 6, 7, 8, 9, 10 or more). Other suitable linker amino acid sequences will be apparent to those skilled in the art. A useful linker is GSGGGG, with the Gly-Ser dipeptide being formed from a BamHI restriction site, which aids cloning and manipulation, and the $(Gly)_4$ tetrapeptide being a typical poly-glycine linker. In addition, protease substrate sequences may also be added (e.g., TEV protease: ENLYFQG).

-A- is an optional N-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking or short peptide sequences which facilitate cloning or purification (e.g., a histidine tag $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is an oligopeptide (e.g., with 1, 2, 3, 4, 5, 6, 7 or 8 amino acids) which provides a N-terminus methionine.

—B— is an optional C-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g., $His_n$ where n=3, 4, 5, 6, 7, 8, 9, 10 or more), or sequences which enhance protein stability. Other suitable C-terminal amino acid sequences will be apparent to those skilled in the art, including that such $His_n$ sequences may be removed when a TEV protease substrate sequence precedes it (e.g., $ENLYFQGHis_n$).

The individual antigens of the immunogenic composition within the multiple epitope fusion antigen (individual —X— moieties) may be from one or more strains or from one or more M types. Where n=2, for instance, $X_2$ may be from the same strain or type as $X_1$ or from a different strain or type. Where n=3, the strains might be (i) $X_1$=$X_2$=$X_3$, (ii) $X_1$=$X_2$ not equal to $X_3$, (iii) $X_1$ not equal to $X_2$=$X_3$, (iv) $X_1$ not equal to $X_2$ not equal to $X_3$, or (v) $X_1$=$X_3$ not equal to $X_2$, and the like.

Where multiple epitope fusion antigens are used, the individual antigens within the fusion protein (i.e., individual —X— moieties) may be from one or more strains. Where n=2, for instance, $X_2$ may be from the same strain as $X_1$ or from a different strain. Where n=3, the strains might be (i) $X_1$=$X_2$=$X_3$ (ii) $X_1$=$X_2$ not equal to $X_3$ (iii) $X_1$ not equal to $X_2$=$X_3$ (iv) $X_1$ not equal to $X_2$ not equal to $X_3$ or (v) $X_1$=$X_3$ not equal to $X_2$, and the like.

Accordingly, in embodiments, antigenic determinants from different Rotavirus species may be present. Representative multiepitope fusion proteins for use in the present disclosure, comprising polypeptides derived from Rotavirus isolates, are discussed below. However, it is to be understood that multiepitope fusion proteins comprising other epitopes derived from Rotavirus genomes or multiepitope fusion proteins comprising different arrangements of epitopes will also find use in immunogenic compositions as disclosed.

In certain embodiments, the fusion protein comprises one or more capsid and/or minor structural polypeptides from one or more isolates of Rotavirus.

In another embodiment, the fusion protein comprises Rotavirus polypeptides from more than one Rotavirus strain.

In all fusions described herein, the viral regions need not be in the order in which they occur naturally. Moreover, each of the regions may be derived from the same or different Rotavirus isolates. The various Rotavirus polypeptides present in the various fusions described above may either be full-length polypeptides or portions thereof.

If desired, the fusion proteins, or the individual components of these proteins, also may contain other amino acid sequences, such as amino acid linkers or signal sequences, as well as ligands useful in protein purification, such as glutathione-S-transferase and staphylococcal protein A.

Nucleic Acids

Nucleic acids for use as disclosed herein, for example, in polypeptide production, may be derived from any of the various regions of a Rotavirus genome. Representative sequences from Rotavirus isolates are listed herein. Thus, nucleic acids for use as disclosed herein include those derived from one or more sequences from any pathogenic Rotavirus species or isolate.

Representative sequences from Rotavirus include SEQ ID NOs:1, 3, 5, 7, 9, 11, 13, 15, 17 and 45.

Any of these sequences, as well as fragments and variants thereof that may be used in nucleic acid immunization to elicit an immune response to a Roravirus will find use in the present methods. Thus, the present disclosure provides variants of the above sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99% or greater, but less than 100% sequence identity thereto. The present disclosure also provides polynucleotides encoding immunogenic fragments of a Rotavirus polypeptide derived from any of the above sequences or a variant thereof. Polynucleotides may also comprise coding sequences for polypeptides which occur naturally or may be artificial sequences which do not occur in nature.

Polynucleotides may contain less than an entire Rotavirus genome, or alternatively may include the sequence of an entire viral genomic RNA. For example, polynucleotides may comprise one or more sequences from the Rotavirus genome. Polynucleotides may also comprise the entire viral genomic Rotavirus or less than the entire viral genomic Rotavirus from multiple species and/or isolates of Rotavirus.

In embodiments, polynucleotides comprise an Rotavirus sequence coding for the full-length polyprotein of a Rotavirus. In other embodiments, polynucleotides comprise one or more portions of the Rotavirus RNA sequence of a Rotavirus.

In another example, a polynucleotide may comprise a nucleotide sequence encoding a portion of a Rotavirus polyprotein.

In embodiments, the polynucleotides comprise sequences encoding one or more capsid proteins of a Rotavirus. For example, polynucleotides may comprise one or more sequences coding for structural proteins (e.g., VP4 and VP7) of a Rotavirus. In certain embodiments, polynucleotides comprise sequences coding for at least two capsid proteins from multiple species and/or isolates of Rotavirus.

In embodiments, polynucleotides comprise one or more Rotavirus sequences coding for the capsid proteins of one or more isolates of Rotavirus. In certain embodiments, polynucleotides comprise one or more sequences coding for the capsid proteins of one or more isolates of Rotavirus.

In embodiments, the present disclosure provides polynucleotides encoding a multiepitope fusion protein as described herein. Multiepitope fusion proteins may comprise sequences from one or more species and/or isolates of Rotavirus.

Nucleic acids according to the instant disclosure may be prepared in many ways (e.g., by chemical synthesis, from genomic or cDNA libraries, from the organism itself, etc.) and may take various forms (e.g., single stranded, double stranded, vectors, probes, and the like). In embodiments, nucleic acids are prepared in substantially pure form (i.e., substantially free from other host cell or non-host cell nucleic acids).

For example, nucleic acids may be obtained by screening cDNA and/or genomic libraries from cells infected with virus, or by deriving the gene from a vector known to include the same. For example, polynucleotides of interest may be isolated from a genomic library derived from viral RNA, present in, for example, hair or blood samples from an infected individual. Alternatively, Rotavirus nucleic acids may be isolated from infected mammals or from biological samples collected from infected individuals. An amplification method such as PCR may be used to amplify polynucleotides from either Rotavirus genomic RNA or cDNA encoding therefor. Alternatively, polynucleotides may be synthesized in the laboratory, for example, using an automatic synthesizer. The nucleotide sequence may be designed with the appropriate codons for the particular amino acid sequence desired. In general, one will select preferred codons for the intended host in which the sequence will be expressed. The complete sequence of the polynucleotide of interest may be assembled from overlapping oligonucleotides prepared by standard methods and assembled into a complete coding sequence. The polynucleotides may be RNA or single- or double-stranded DNA. In embodiments, the polynucleotides are isolated free of other components, such as proteins and lipids.

Thus, particular nucleotide sequences may be obtained from vectors harboring the desired sequences or synthesized completely or in part using various oligonucleotide synthesis techniques known in the art, such as site-directed mutagenesis and polymerase chain reaction (PCR) techniques where appropriate. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. Primer sequences may include, but are not limited to, SEQ ID NOs:19-44 and 47-52.

Production of Immunogenic Polypeptides

Polypeptides described herein may be prepared in any suitable manner (e.g., recombinant expression, purification from cell culture, chemical synthesis, and the like) and in various forms (e.g., native, fusions, non-glycosylated, lipidated, and the like). Such polypeptides include naturally-occurring polypeptides, recombinantly produced polypeptides, synthetically produced polypeptides, or polypeptides produced by a combination of these methods. Means for preparing such polypeptides are well understood in the art. Polypeptides are prepared in substantially pure form (i.e., substantially free from other host cell or non-host cell proteins).

Polypeptides may be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid may then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like. Typical solid supports are cross-linked polymeric supports. These may include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptides of the present disclosure may also be chemically prepared by other methods such as by the method of simultaneous multiple peptide synthesis.

Alternatively, the above-described immunogenic polypeptides, polyproteins, and multiepitope fusion proteins may be produced recombinantly. Once coding sequences for the desired proteins have been isolated or synthesized, they may be cloned into any suitable vector or replicon for expression. Numerous cloning vectors are known to those of skill in the art, and the selection of an appropriate cloning vector is a matter of choice. A variety of bacterial, yeast, plant, mammalian and insect expression systems are available in the art and any such expression system may be used. Optionally, a polynucleotide encoding these proteins may be translated in a cell-free translation system. Such methods are well known in the art.

Examples of recombinant DNA vectors for cloning and host cells which they may transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells).

Insect cell expression systems, such as baculovirus systems, may also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego, CA ("MaxBac" kit).

Plant expression systems may also be used to produce the immunogenic proteins. Generally, such systems use virus-based vectors to transfect plant cells with heterologous genes.

Viral systems, such as a vaccinia based infection/transfection system, will also find use with the subject matter as disclosed herein. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene may be placed under the control of a promoter, ribosome binding site (for bacterial expression) and, optionally, an operator (collectively referred to herein as "control" elements), so that the DNA sequence encoding the desired immunogenic polypeptide is transcribed into RNA in the host cell transformed by a vector containing this expression construction. The coding sequence may or may not contain a signal peptide or leader sequence. With the present subject matter as disclosed herein, both the naturally occurring signal peptides or heterologous sequences may be used. Leader sequences may be removed by the host in post-translational processing. See, e.g., U.S. Pat. Nos. 4,431,739; 4,425,437; 4,338,397, each herein incorporated by reference in their entireties. Such sequences include, but are not limited to, the tpa leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence may be cloned directly into an expression vector which already contains the control sequences and an appropriate restriction site.

In embodiments, it may be necessary to modify the coding sequence so that it may be attached to the control sequences with the appropriate orientation; i.e., to maintain the proper reading frame. It may also be desirable to produce mutants or analogs of the immunogenic polypeptides. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), as well as others. Similarly, bacterial hosts such as *E. coli*, *Bacillus subtilis*, and *Streptococcus* spp., will find use with the present expression constructs. Yeast hosts useful with the subject matter as disclosed include, inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni.*

Depending on the expression system and host selected, the proteins as disclosed herein are produced by growing host cells transformed by an expression vector described above under conditions whereby the protein of interest is expressed. The selection of the appropriate growth conditions is within the skill of the art. The cells are then disrupted, using chemical, physical or mechanical means, which lyse the cells yet keep the Rotavirus immunogenic polypeptides substantially intact. Intracellular proteins may also be obtained by removing components from the cell wall or membrane, e.g., by the use of detergents or organic solvents, such that leakage of the immunogenic polypeptides occurs.

For example, methods of disrupting cells for use with the subject matter as disclosed herein include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced Rotavirus immunogenic polypeptides are further purified, using standard purification techniques such as but not limited to, column chromatography, ion-exchange chromatography, size-exclusion chromatography, electrophoresis, HPLC, immunoabsorbent techniques, affinity chromatography, immunoprecipitation, and the like.

For example, one method for obtaining the intracellular Rotavirus immunogenic polypeptides as disclosed herein involves affinity purification, such as by immunoaffinity chromatography using specific antibodies. The choice of a suitable affinity resin is within the skill in the art. After affinity purification, immunogenic polypeptides may be further purified using conventional techniques well known in the art, such as by any of the techniques described above.

It may be desirable to produce multiple polypeptides simultaneously (e.g., structural and/or nonstructural proteins from one or more viral strains or viral polypeptides in combination with polypeptide adjuvants). Production of two or more different polypeptides may readily be accomplished by e.g., co-transfecting host cells with constructs encoding the different polypeptides. Co-transfection may be accomplished either in trans or cis, i.e., by using separate vectors or by using a single vector encoding the polypeptides. If a single vector is used, expression of the polypeptides may be driven by a single set of control elements or, alternatively, the sequences coding for the polypeptides may be present on the vector in individual expression cassettes, regulated by individual control elements.

The polypeptides described herein may be attached to a solid support. The solid supports which may be used in the practice with the subject matter as disclosed herein include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more Rotavirus antigens) under suitable binding conditions such that the component is sufficiently immobilized to the support. Sometimes, immobilization of the antigen to the support may be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that may be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art.

If desired, polypeptides may be labeled using conventional techniques. Suitable labels include fluorophores, chromophores, radioactive atoms (particularly $^{32}P$ and $^{125}I$, electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. A single label or a combination of labels may be used in the as disclosed herein.

Once formulated, the compositions as disclosed herein may be administered directly to the subject (e.g., as described above) or, alternatively, delivered ex vivo, to cells derived from the subject, using methods such as those described above.

Immunogenic Compositions

The present disclosure also provides compositions comprising one or more of the immunogenic polypeptides and/or polyproteins multiepitope fusion proteins described herein. Different polypeptides, polyproteins, and multiple epitope fusion proteins may be mixed together in a single formulation. Within such combinations, an antigen of the immunogenic composition may be present in more than one polypeptide, or multiple epitope polypeptide, or polyprotein.

The immunogenic compositions may comprise a mixture of polypeptides, which in turn may be delivered using the same or different vehicles. Antigens may be administered individually or in combination, in e.g., prophylactic (i.e., to prevent infection) or therapeutic (to treat infection) immunogenic compositions. The immunogenic composition may be given more than once (e.g., a "prime" administration followed by one or more "boosts") to achieve the desired effects. The same composition may be administered in one or more priming and one or more boosting steps. Alternatively, different compositions may be used for priming and boosting.

The immunogenic compositions will generally include one or more "pharmaceutically acceptable excipients or vehicles" such as water, saline, glycerol, ethanol, and the like. Additionally, auxiliary substances, such as wetting or emulsifying agents, pH buffering substances, and the like, may be present in such vehicles.

Immunogenic compositions will typically, in addition to the components mentioned above, comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, and the like. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472.

Pharmaceutically acceptable salts may also be used in compositions as disclosed herein, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, *tetanus* toxoid, and other proteins well known to those of skill in the art. Compositions as disclosed may also contain liquids or excipients, such as water, saline, glycerol, dextrose, ethanol, or the like, singly or in combination, as well as substances such as wetting agents, emulsifying agents, or pH buffering agents. Antigens may also be adsorbed to, entrapped within or otherwise associated with liposomes and particulate carriers such as PLG.

Antigens may be conjugated to a carrier protein in order to enhance immunogenicity. This is particularly useful in compositions in which a saccharide or carbohydrate antigen is used.

Carrier proteins may include, but are not limited to, bacterial toxins or toxoids, such as diphtheria or *tetanus* toxoids. The $CRM_{197}$ diphtheria toxoid may be used. Other carrier polypeptides include the *N. meningitidis* outer membrane protein (EP-A-0372501), synthetic peptides (EP-A-0378881 and EP-A-0427347), heat shock proteins (WO 93/17712 and WO 94/03208), *pertussis* proteins (WO 98/58668 and EP-A-0471177), protein D from *H. influenzae* (WO 00/56360), cytokines (WO 91/01146), lymphokines, hormones, growth factors, toxin A or B from *C. difficile* (WO 00/61761), iron-uptake proteins, such as transferring (WO 01/72337), etc. Where a mixture comprises capsular saccharide from both serigraphs A and C, it may be that the ratio (w/w) of MenA saccharide:MenC saccharide is greater than 1 (e.g., 2:1, 3:1, 4:1, 5:1, 10:1 or higher). Different saccharides may be conjugated to the same or different type of carrier protein. Any suitable conjugation reaction may be used, with any suitable linker where necessary.

Immunogenic compositions, including vaccines as disclosed may be administered in conjunction with other immunoregulatory agents. For example, a vaccine as disclosed herein may include an adjuvant. Adjuvants include, but are not limited to, one or more of the following types of adjuvants described below.

Mineral Containing Compositions

Mineral containing compositions suitable for use as adjuvants disclosed herein include mineral salts, such as aluminum salts and calcium salts. Salts as disclosed herein includes mineral salts such as hydroxides (e.g., oxyhydroxides), phosphates (e.g., hydroxyphosphates, orthophosphates), sulfates, and the like, or mixtures of different mineral compounds (e.g., a mixture of a phosphate and a hydroxide adjuvant, optionally with an excess of the phosphate), with the compounds taking any suitable form (e.g., gel, crystalline, amorphous, and the like). The mineral containing compositions may also be formulated as a particle of metal salt (WO00/23105).

Aluminum salts may be included in vaccines such that the dose of $Al^{3+}$ is between 0.2 and 1.0 mg per dose.

In embodiments, the aluminum based adjuvant for use as disclosed is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2/g$. Alternatively, aluminum phosphate adjuvant ($AlPO_4$) or aluminum hydroxyphosphate, which contains phosphate groups in place of some or all of the hydroxyl groups of aluminum hydroxide adjuvant is provided. In embodiments, aluminum phosphate adjuvants provided herein are amorphous and soluble in acidic, basic and neutral media.

In embodiments, the adjuvant as disclosed herein comprises both aluminum phosphate and aluminum hydroxide. In one aspect, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (i.e., 11.4). Alternatively, pretreatment of aluminum hydroxide with phosphate lowers its isoelectric point, making it a preferred adjuvant for more basic antigens.

Oil-Emulsions

Oil-emulsion compositions suitable for use as adjuvants may include squalene-water emulsions, such as MF59 (5% Squalene, 0.5% TWEEN 80™, and 0.5% SPAN 85™, formulated into submicron particles using a microfluidizer). See WO90/14837. MF59 is used as the adjuvant in the FLUAD™ influenza virus trivalent subunit vaccine.

Particularly adjuvants for use in the compositions are submicron oil-in-water emulsions. Submicron oil-in-water emulsions for use herein may be squalene/water emulsions optionally containing varying amounts of MTP-PE, such as a submicron oil-in-water emulsion containing 4-5% w/v squalene, 0.25-1.0% w/v TWEEN80™ (polyoxyelthylenesorbitan monooleate), and/or 0.25-1.0% SPAN85™ (sorbitan trioleate), and, optionally, N-acetylmuramyl-L-alanyl-D-isoglutaminyl-L-alanine-2-(.beta.-2'-dipalmito-yl-sn-glycero-3-huydroxyphosphophoryloxy)-ethylamine (MTP-PE), for example, the submicron oil-in-water emulsion known as "MF59" (International Publication No. WO90/14837; U.S. Pat. Nos. 6,299,884 and 6,451,325.) MF59 contains 4-5% w/v Squalene (e.g., 4.3%), 0.25-0.5% w/v TWEEN80™, and 0.5% w/v SPAN85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 g/dose, 0-250 g/dose and 0-100 g/dose. As used herein, the term "MF59-0" refers to the above submicron oil-in-water emulsion lacking MTP-PE, while the term MF59-MTP denotes a formulation that contains MTP-PE. For instance, "MF59-100" contains 100 .mu.g MTP-PE per dose, and so on. MF69, another submicron oil-in-water emulsion for use herein, contains 4.3% w/v squalene, 0.25% w/v TWEEN80™, and 0.75% w/v SPAN85™ and optionally MTP-PE. Yet another submicron oil-in-water emulsion is MF75, also known as SAF, containing 10% squalene, 0.4% TWEEN80™, 5% pluronic-blocked polymer L121, and thr-MDP, also microfluidized into a submicron emulsion. MF75-MTP denotes an MF75 formulation that includes MTP, such as from 100-400 g MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) may also be used as adjuvants.

Saponin Formulations

Saponin formulations, may also be used as adjuvants. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins may also be commercially obtained from *Smilax ornata* (sarsaparilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. In embodiments, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols may be used to form unique particles called Immunostimulating Complexes (ISCOMs). ISCOMs typically also include a phospholipid such as phosphatidylethanolamine or phosphatidylcholine. Any known saponin may be used in ISCOMs. In embodiments, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

Bacterial or Microbial Derivatives

Adjuvants suitable for use as disclosed herein include bacterial or microbial derivatives such as:

(1) Non-Toxic Derivatives of Enterobacterial Lipopolysaccharide (LPs)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. One "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g., RC-529.

(2) Lipid A Derivatives

Lipid A derivatives include derivatives of lipid A from *Escherichia coli* such as OM-174.

(3) Immunostimulatory Oligonucleotides

Immunostimulatory oligonucleotides suitable for use as adjuvants may include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's may include nucleotide modifications/analogs such as phosphorothioate modifications and may be double-stranded or single-stranded. Optionally, the guanosine may be replaced with an analog such as 2'-deoxy-7-deazaguanosine.

The CpG sequence may be directed to TLR9, such as the motif GTCGTT or TTCGTT. The CpG sequence may be specific for inducing a Th1 immune response, such as a CpG-A ODN, or it may be more specific for inducing a B cell response, such a CpG-B ODN. In embodiments, the CpG is a CpG-A ODN.

In embodiments, the CpG oligonucleotide may be constructed so that the 5' end is accessible for receptor recognition. Optionally, two CpG oligonucleotide sequences may be attached at their 3' ends to form "immunomers."

(4) ADP-Ribosylating Toxins and Detoxified Derivatives Thereof.

Bacterial ADP-ribosylating toxins and detoxified derivatives thereof may be used as adjuvants. In embodiments, the protein may be derived from *E. coli* (i.e., *E. coli* heat labile enterotoxin "LT), cholera ("CT"), or *pertussis* ("PT"). The use of detoxified ADP-ribosylating toxins as mucosal adjuvants is described in WO95/17211 and as parenteral adjuvants in WO98/42375. In embodiments, the adjuvant is a detoxified LT mutant such as LT-K63, LT-R72, and LTR192G.

Bioadhesives and Mucoadhesives

Bioadhesives and mucoadhesives may also be used as adjuvants. Suitable bioadhesives include esterified hyaluronic acid microspheres or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants. E.g., WO99/27960.

Muramyl Peptides

Examples of muramyl peptides suitable for use as adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-s-n-glycero-3-hydroxyphosphoryloxy)-ethylamine MTP-PE).

Imidazoquinoline Compounds.

Examples of imidazoquinoline compounds suitable for use as adjuvants include Imiquimod and its analogues (see, e.g., U.S. Pat. Nos. 4,689,338, 5,389,640, 5,268,376, 4,929, 624, 5,266,575, 5,352,784, 5,494,916, 5,482,936, 5,346,905, 5,395,937, 5,238,944, and 5,525,612).

Thiosemicarbazone Compounds.

Examples of thiosemicarbazone compounds, as well as methods of formulating, manufacturing, and screening for compounds all suitable for use as adjuvants include those described in WO04/60308. The thiosemicarbazones are particularly effective in the stimulation of human peripheral blood mononuclear cells for the production of cytokines, such as TNF-α

Tryptanthrin Compounds.

Examples of tryptanthrin compounds, as well as methods of formulating, manufacturing, and screening for compounds all suitable for use as adjuvants as disclosed herein include those described in WO04/64759. The tryptanthrin compounds are particularly effective in the stimulation of human peripheral blood mononuclear cells for the production of cytokines, such as TNF-α.

Combinations of aspects of one or more of the adjuvants identified above may be applied to the compositions as disclosed herein. For example, the following adjuvant compositions may be used:

(1) a saponin and an oil-in-water emulsion (WO99/11241); (2) a saponin (e.g., QS21)+a non-toxic LPS derivative (e.g., 3dMPL) (see WO94/00153); (3) a saponin (e.g., QS21)+a non-toxic LPS derivative (e.g., 3dMPL)+a cholesterol; (4) a saponin (e.g., QS21)+3dMPL+IL-12 (optionally+a sterol) (WO98/57659); (5) combinations of 3dMPL with, for example, QS21 and/or oil-in-water emulsions (See European patent applications 0835318, 0735898 and 0761231); (6) SAF, containing 10% Squalane, 0.4% TWEEN80™, 5% pluronic-block polymer L121, and thr-MDP, either microfluidized into a submicron emulsion or vortexed to generate a larger particle size emulsion. (7) RIBI™ adjuvant system (RAS), (Ribi Immunochem) containing 2% Squalene, 0.2% TWEEN80™, and one or more bacterial cell wall components from the group consisting of monophosphorylipid A (MPL), trehalose dimycolate (TDM), and cell wall skeleton (CWS), MPL+CWS (DETOX™); and (8) one or more mineral salts (such as an aluminum salt)+a non-toxic derivative of LPS (such as 3dPML). (9) one or more mineral salts (such as an aluminum salt) and one or more immunostimulatory oligonucleotides (such as a nucleotide sequence including a CpG motif) and one or more detoxified ADP-ribosylating toxins (such as LT-K63 and LT-R72), (10) inulin and inulin acetate formulations (see, e.g., WO 2013/110050, herein incorporated in its entirety).

Additional Antigens

Compositions of the as disclosed herein optionally may comprise one or more additional polypeptide antigens which are not derived from Rotavirus proteins. Such antigens include bacterial, viral, or parasitic antigens.

In some embodiments, Rotavirus antigens are combined with one or more antigens including, but not limited to, antigens derived from a bacteria or virus, such as Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV), *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (*Tetanus*), *Corynebacterium diphtheriae* (Diphtheria), *Haemophilus influenzae* B (Hib), *Pseudomonas aeruginosa, Streptococcus agalactiae* (Group B *Streptococcus*), and *E. coli.*

In other embodiments, Rotavirus antigens are combined with one or more antigens including, but not limited to, *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (*Tetanus*), *Corynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Chlamydia pneumoniae*, Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV).

In other embodiments, Rotavirus antigens are combined with one or more antigens which are useful in a vaccine designed to protect individuals against pathogens that cause diarrheal diseases. Such antigens include, but are not limited to, rotavirus, *Shigella* spp., enterotoxigenic *Escherichia coli* (ETEC), *Vibrio cholerae*, and *Campylobacter jejuni* antigens. In embodiments, one or more Norovirus antigens may be derived from Norwalk virus, Snow Mountain virus, and/or Hawaii virus are combined with a rotavirus antigen in an immunogenic composition.

Antigens which may find use with the present compositions include, but are not limited to, one or more of the following antigens set forth below, or antigens derived from one or more of the pathogens set forth below:

Bacterial Antigens

Suitable Bacterial antigens as disclosed herein include proteins, polysaccharides, lipopolysaccharides, and outer membrane vesicles which may be isolated, purified or derived from a bacteria. In addition, bacterial antigens may include bacterial lysates and inactivated bacteria formulations. Bacteria antigens may be produced by recombinant expression. Bacterial antigens include epitopes which may be exposed on the surface of the bacteria during at least one stage of its life cycle. Bacterial antigens may be conserved across multiple serotypes. Bacterial antigens include antigens derived from one or more of the bacteria set forth below as well as the specific antigens examples identified below.

*Neisseria meningitides: Meningitides* antigens may include proteins (such as those identified in References 1-7), saccharides (including a polysaccharide, oligosaccharide or lipopolysaccharide), or outer-membrane vesicles purified or derived from *N. meningitides* serogroup such as A, C, W135, Y, and/or B. *Meningitides* protein antigens may be selected from adhesions, autotransporters, toxins, Fe acquisition proteins, and membrane associated proteins (e.g., integral outer membrane protein).

*Streptococcus pneumoniae: Streptococcus pneumoniae* antigens may include a saccharide (including a polysaccharide or an oligosaccharide) and/or protein from *Streptococcus pneumoniae*. Saccharide antigens may be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens may be selected from a protein identified in WO 98/18931, WO 98/18930, U.S. Pat. Nos. 6,699,703, 6,800,744, WO 97/43303, and WO 97/37026. *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens may include a protein identified in WO 02/34771 or WO 2005/032582 (including GAS 40), fusions of fragments of GAS M proteins (including those described in WO 02/094851), fibronectin binding protein (Sfb1), Streptococcal heme-associated protein (Shp), and Streptolysin S (SagA).

*Moraxella catarrhalis: Moraxella* antigens include antigens identified in WO 02/18595 and WO 99/58562, outer membrane protein antigens (HMW-OMP), C-antigen, and/or LPS.

*Bordetella pertussis: Pertussis* antigens include *pertussis* holotoxin (PT) and filamentous haemagglutinin (FHA) from *B. pertussis*, optionally also combination with pertactin and/or agglutinogens 2 and 3 antigen.

*Staphylococcus aureus*: Staph aureus antigens include *S. aureus* type 5 and 8 capsular polysaccharides optionally conjugated to nontoxic recombinant *Pseudomonas aeruginosa* exotoxin A, such as STAPHVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin).

*Staphylococcus epidermis: S. epidermidis* antigens include slime-associated antigen (SAA).

*Clostridium tetani* (*Tetanus*): *Tetanus* antigens include *tetanus* toxoid (TT), may be used as a carrier protein in conjunction/conjugated with the compositions of the present disclosure.

*Corynebacterium diphtheriae* (Diphtheria): Diphtheria antigens include diphtheria toxin, including detoxified, such as $CRM_{197}$. Additionally, antigens capable of modulating, inhibiting or associated with ADP ribosylation are contemplated for combination/co-administration/conjugation with the compositions of the present disclosure. The diphtheria toxoids may be used as carrier proteins.

*Haemophilus influenzae* B (Hib): Hib antigens include a Hib saccharide antigen.

*Pseudomonas aeruginosa: Pseudomonas* antigens include endotoxin A, Wzz protein, *P. aeruginosa* LPS, more particularly LPS isolated from PAO1 (05 serotype), and/or Outer Membrane Proteins, including Outer Membrane Proteins F (OprF).

*Legionella pneumophila*. Bacterial antigens may be derived from *Legionella pneumophila*.

*Streptococcus agalactiae* (Group B *Streptococcus*): Group B *Streptococcus* antigens include a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neisseria gonorrhoeae: Gonorrhoeae* antigens include Por (or porin) protein, such as PorB, a transferring binding protein, such as TbpA and TbpB, a opacity protein (such as Opa), a reduction-modifiable protein (Rmp), and outer membrane vesicle (OMV) preparations (see e.g., WO99/24578, WO99/36544, WO99/57280, WO02/079243).

*Chlamydia trachomatis: Chlamydia trachomatis* antigens include antigens derived from serotypes A, B, Ba and C (agents of trachoma, a cause of blindness), serotypes $L_1$, $L_2$ & $L_3$ (associated with Lymphogranuloma venereum), and serotypes, D-K. *Chlamydia* trachomas antigens may also include an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include TmpA antigen.

*Haemophilus ducreyi* (causing cancroid): *Ducreyi* antigens include outer membrane protein (DsrA).

*Enterococcus faecalis* or *Enterococcus faecium*: Antigens include a trisaccharide repeat or other *Enterococcus* derived antigens provided in U.S. Pat. No. 6,756,361.

*Helicobacter pylori: H. pylori* antigens include Cag, Vac, Nap, HopX, HopY and/or urease antigen.

*Staphylococcus saprophyticus*: Antigens include the 160 kDa hemagglutinin of *S. saprophyticus* antigen.

*Yersinia enterocolitica* Antigens include LPS.

*E. coli: E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC).

*Bacillus anthracis* (anthrax): *B. anthracis* antigens are optionally detoxified and may be selected from A-components (lethal factor (LF) and edema factor (EF)), both of which may share a common B-component known as protective antigen (PA).

*Yersinia pestis* (plague): Plague antigens include F1 capsular antigen.

*Mycobacterium tuberculosis*: Tuberculosis antigens include lipoproteins, LPS, BCG antigens, a fusion protein of antigen 85B (Ag85B) and/or ESAT-6 optionally formulated in cationic lipid vesicles, *Mycobacterium tuberculosis* (Mtb) isocitrate dehydrogenase associated antigens, and/or MPT51 antigens.

*Rickettsia*: Antigens include outer membrane proteins, including the outer membrane protein A and/or B (OmpB).

*Listeria monocytogenes*. Bacterial antigens may be derived from *Listeria monocytogenes*.

*Chlamydia pneumoniae*: Antigens include those identified in WO 02/02606.

*Vibrio cholerae*: Antigens include proteinase antigens, LPS, particularly lipopolysaccharides of *Vibrio cholerae* II, 01 Inaba 0-specific polysaccharides, *V. cholera* 0139, antigens of IEM108 vaccine, and/or Zonula occludens toxin (Zot).

*Salmonella typhi* (typhoid fever): Antigens include capsular polysaccharides, including conjugates (Vi, i.e., vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 VlsE Antigenic Variation Protein.

*Porphyromonas gingivalis*: Antigens include *P. gingivalis* outer membrane protein (OMP).

*Klebsiella*: Antigens include an OMP, including OMP A, or a polysaccharide optionally conjugated to *tetanus* toxoid.

Further bacterial antigens of the instant disclosure may be capsular antigens, polysaccharide antigens or protein antigens of any of the above. Further bacterial antigens may also include an outer membrane vesicle (OMV) preparation. Additionally, antigens include live, attenuated, and/or purified versions of any of the aforementioned bacteria. The antigens of the present disclosure may be derived from gram-negative or gram-positive bacteria. The antigens of the present disclosure may be derived from aerobic or anaerobic bacteria.

Additionally, any of the above bacterial-derived saccharides (polysaccharides, LPS, LOS or oligosaccharides) may be conjugated to another agent or antigen, such as a carrier protein (for example $CRM_{197}$). Such conjugation may be direct conjugation effected by reductive amination of carbonyl moieties on the saccharide to amino groups on the protein, as provided in U.S. Pat. No. 5,360,897. Alternatively, the saccharides may be conjugated through a linker, such as, with succinamide or other linkages.

Viral Antigens

Viral antigens suitable for use in the compositions as disclosed include purified subunit formulations, viral proteins which may be isolated, purified or derived from a virus, and Virus Like Particles (VLPs). Viral antigens may be derived from viruses propagated on cell culture or other substrate. Alternatively, viral antigens may be expressed recombinantly. Viral antigens include epitopes which are exposed on the surface of the virus during at least one stage of its life cycle. Viral antigens may be conserved across multiple serotypes or isolates. Viral antigens include antigens derived from one or more of the viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). In embodiments, antigens include HA and NA.

Influenza antigens may be derived from interpandemic (annual) flu strains. Alternatively, influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. In embodiments, the Pneumovirus is RSV Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Pneumovirus antigens may include F, G and M. Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. In embodiments, the Paramyxovirus is PIV or Mumps. Paramyxovirus antigens may be selected from one or more of the following proteins: Hemagglutinin-Neuraminidase (HN), Fusion proteins F1 and F2, Nucleoprotein (NP), Phosphoprotein (P), Large protein (L), and Matrix protein (M). Paramyxovirus proteins may include HN, F1 and F2. Paramyxovirus antigens may also be formulated in or derived from chimeric viruses. For example, chimeric RSV/PIV viruses may comprise components of both RSV and PIV Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are may be used.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In embodiments, the Enterovirus may be poliovirus. Enterovirus antigens may include one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from an Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, may be used. Togavirus antigens may be selected from E1, E2, E3, C, NSP-1, NSPO-2, NSP-3 or NSP-4. Togavirus antigens include E1, E2 or E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens may include PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the nonstructural regions.

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens may be derived from Calciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). In embodiments, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (e.g., p55 gag and gp140v delete). HIV antigens may be derived from one or more of the following strains: $HIV_{IIIb}$, $HIV_{SF2}$, $HIV_{LAV}$, $HIV_{LAI}$, $HIV_{MN}$, HIV-$1_{CM235}$, HIV-$1_{US4}$.

Reovirus: Viral antigens may be derived from a Reovirus, such as an Orthoreovirus, a Rotavirus, an Orbivirus, or a Coltivirus. Reovirus antigens may be selected from structural proteins λ1, λ2, λ3, μ1, μ2, σ1, σ2, or σ3, or nonstructural proteins σNS, μNS, or σ1s. Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Rotavirus antigens may include VP4 (or the cleaved product VP5 and VP8), and VP7. See, e.g., WO 2005/021033, WO 2003/072716, WO 2002/11540, WO 2001/12797, WO 01/08495, WO 00/26380, WO 02/036172; herein incorporated by reference in their entireties.

Parvovirus: Viral antigens may be derived from a Parvovirus, such as Parvovirus B19. Parvovirus antigens may be selected from VP-1, VP-2, VP-3, NS-1 and NS-2. In embodiments, the Parvovirus antigen is capsid protein VP-2.

Delta hepatitis virus (HDV): Viral antigens may be derived HDV, particularly .delta.-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins (α), early proteins (β), and late proteins (γ). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. In embodiments, HPV antigens are derived from serotypes 6, 11, 16 or 18. HPV antigens may include capsid proteins (L1) and (L2), or E1-E7, or fusions thereof. Polyomyavirus viruses include BK virus and JK virus. Polyomavirus antigens may be selected from VP1, VP2 or VP3.

Circovirus: Antigens may be derived from Circoviruses, such as Porcine circovirus (PCV) 1, PCV 2, PCV 3, and PCV 4.

Fungal Antigens

Suitable fungal antigens may be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme.*

Fungal pathogens may be derived from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp., *Mucor* spp., *Absidia* spp., *Mortierella* spp., *Cunninghamella* spp., *Saksenaea* spp., *Alternaria* spp., *Curvularia* spp., *Helminthosporium* spp., *Fusarium* spp., *Aspergillus* spp., *Penicillium* spp., *Monolinia* spp., *Rhizoctonia* spp., *Paecilomyces* spp., *Pithomyces* spp., and *Cladosporium* spp.

Processes for producing a fungal antigens are well known in the art (see U.S. Pat. No. 6,333,164). In one method, a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

Respiratory Antigens

The compositions of the as disclosed herein may include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacteria which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis*, and *Moraxella catarrhalis*. Examples of specific antigens derived from these pathogens are described above.

The immunogenic compositions as disclosed herein may be prepared in various forms. For example, the compositions may be prepared as injectables, either as liquid solutions or suspensions. Solid forms suitable for solution in, or suspension in, liquid vehicles prior to injection may also be prepared (e.g., a lyophilized composition or a spray-freeze dried composition). The composition may be prepared for topical administration e.g., as an ointment, cream or powder. The composition may be prepared for oral administration e.g., as a tablet or capsule or as a spray. The composition may be prepared for pulmonary administration e.g., as an inhaler, using a fine powder or a spray. The composition may be prepared as a suppository or pessary. The composition may be prepared for nasal, aural or ocular administration e.g., as drops. Preparation of such pharmaceutical compositions is within the general skill of the art. See, e.g., Remington's Pharmaceutical Sciences, Mack Publishing Company, Easton, Pa., 18th edition, 1990.

The composition may be in kit form, designed such that a combined composition is reconstituted just prior to administration to a patient. Such kits may comprise one or more Rotavirus antigens or nucleic acids encoding such antigens in liquid form, and any of the additional antigens and adjuvants as described herein.

Immunogenic compositions comprising polypeptide antigens as disclosed are vaccine compositions. The pH of such compositions is between 6 and 8, about 7. The pH may be maintained by the use of a buffer. The composition may be sterile and/or pyrogen-free. The composition may be isotonic with respect to the subject. Vaccines according to the instant disclosure may be used either prophylactically or therapeutically, but will typically be prophylactic and may be used to treat animals (including farm, game, companion and laboratory mammals).

Immunogenic compositions used as vaccines comprise an immunologically effective amount of antigen(s) and/or nucleic acids encoding antigen(s), as well as any other components, as needed. By "immunologically effective amount," it is meant that the administration of that amount to an individual, either in a single dose or as part of a series, is effective for treatment or prevention. This amount varies depending upon the health and physical condition of the individual to be treated, age, the taxonomic group of individual to be treated (e.g., swine, cattle, and the like), the capacity of the individual's immune system to synthesize antibodies, the degree of protection desired, the formulation of the vaccine, the treating veterinarian's assessment of the medical situation, and other relevant factors. It is expected that the amount will fall in a relatively broad range that may be determined through routine trials.

Administration

Compositions of as disclosed herein will generally be administered directly to a subject. Direct delivery may be accomplished by parenteral injection (e.g., subcutaneously, intraperitoneally, intravenously, intramuscularly, or to the interstitial space of a tissue), or mucosally, such as by rectal, oral (e.g., tablet, spray), vaginal, topical, transdermal (see, e.g., WO99/27961) or transcutaneous (see e.g., WO02/074244 and WO02/064162), intranasal (see, e.g., WO03/028760), ocular, aural, pulmonary or other mucosal administration. Immunogenic compositions may also be administered topically by direct transfer to the surface of the skin. Topical administration may be accomplished without utilizing any devices, or by contacting naked skin with the immunogenic composition utilizing a bandage or a bandage-like device (see, e.g., U.S. Pat. No. 6,348,450).

In embodiments, the mode of administration may be parenteral, mucosal or a combination of mucosal and parenteral immunizations. In one aspect, the mode of administration is parenteral, mucosal or a combination of mucosal and parenteral immunizations in a total of 1-2 vaccinations 1-3 weeks apart. In one aspect, the route of administration includes but is not limited to oral delivery, intra-muscular delivery and a combination of oral and intra-muscular delivery.

It has already been demonstrated that mucosal and systemic immune responses to antigens, such as *Helicobacter pylori* antigens may be enhanced through mucosal priming followed by systemic boosting immunizations. In embodiments, the method for treating an infection by a Rotavirus, comprises mucosally administering to a subject in need thereof a first immunogenic composition comprising Rotavirus antigens followed by parenterally administering a therapeutically effective amount of a second immunogenic composition comprising Rotavirus antigens.

The immunogenic composition may be used to elicit systemic and/or mucosal immunity, to elicit an enhanced systemic and/or mucosal immunity.

In embodiments, the immune response is characterized by the induction of a serum IgG and/or intestinal IgA immune response.

As noted above, prime-boost methods may be employed where one or more gene delivery vectors and/or polypeptide antigens are delivered in a "priming" step and, subsequently, one or more second gene delivery vectors and/or polypeptide antigens are delivered in a "boosting" step. In certain embodiments, priming and boosting with one or more gene delivery vectors or polypeptide antigens described herein is followed by additional boosting with one or more polypeptide-containing compositions (e.g., polypeptides comprising Rotavirus antigens).

In any method involving co-administration, the various compositions may be delivered in any order. Thus, in embodiments including delivery of multiple different compositions or molecules, the nucleic acids need not be all delivered before the polypeptides. For example, the priming step may include delivery of one or more polypeptides and the boosting comprises delivery of one or more nucleic acids and/or one or more polypeptides. Multiple polypeptide administrations may be followed by multiple nucleic acid administrations or polypeptide and nucleic acid administrations may be performed in any order. Thus, one or more of the gene delivery vectors described herein and one or more of the polypeptides described herein may be co-administered in any order and via any administration route. Therefore, any combination of polynucleotides and polypeptides described herein may be used to elicit an immune reaction.

Dosage Regime

Dosage treatment may be according to a single dose schedule or a multiple dose schedule. Multiple doses may be used in a primary immunization schedule and/or in a booster immunization schedule. In a multiple dose schedule, the various doses may be given by the same or different routes, e.g., a parenteral prime and mucosal boost, a mucosal prime and parenteral boost, and the like.

In embodiments, the dosage regime enhances the avidity of the antibody response leading to antibodies with a neutralizing characteristic. An in-vitro neutralization assay may be used to test for neutralizing antibodies.

There is a strong case for a correlation between serum antibody levels and protection from disease caused by Rotavirus.

Tests to Determine the Efficacy of an Immune Response

One way of assessing efficacy of therapeutic treatment involves monitoring infection after administration of a composition of the as disclosed. One way of assessing efficacy of prophylactic treatment involves monitoring immune responses against the antigens in the compositions of the as disclosed after administration of the composition.

Another way of assessing the immunogenicity of the component proteins of the immunogenic compositions of the present disclosure is to express the proteins recombinantly and to screen patient sera or mucosal secretions by immunoblot. A positive reaction between the protein and the patient serum indicates that the patient has previously mounted an immune response to the protein in question—that is, the protein is an immunogen. This method may also be used to identify immunodominant proteins and/or epitopes.

Another way of checking efficacy of therapeutic treatment involves monitoring infection after administration of the compositions of the present disclosure. One way of checking efficacy of prophylactic treatment involves monitoring immune responses both systemically (such as monitoring the level of IgG1 and IgG2a production) and mucosally (such as monitoring the level of IgA production) against the antigens in the compositions of the present disclosure after administration of the composition. Typically, serum specific antibody responses are determined post-immunization but pre-challenge whereas mucosal specific antibody body responses are determined post-immunization and post-challenge.

The immunogenic compositions of the present disclosure may be evaluated in in vitro and in vivo animal models prior to host. Particularly useful mouse models include those in which intraperitoneal immunization is followed by either intraperitoneal challenge or intranasal challenge.

The efficacy of immunogenic compositions of the present disclosure may also be determined in vivo by challenging animal models of infection, e.g., guinea pigs or mice or rhesus macaques, with the immunogenic compositions. The immunogenic compositions may or may not be derived from the same strains as the challenge strains. In embodiments, the immunogenic compositions may be derivable from the same strains as the challenge strains.

In vivo efficacy models include but are not limited to: (i) A murine infection model using human strains; (ii) a murine disease model which is a murine model using a mouse-adapted strain, such as strains which are particularly virulent in mice and (iii) a primate model using human isolates. A human challenge model, which is supported by the NIH and Center for Disease Control (CDC) is also available.

The immune response may be one or both of a TH1 immune response and a TH2 response. The immune response may be an improved or an enhanced or an altered immune response. The immune response may be one or both of a systemic and a mucosal immune response. In embodiments, the immune response is an enhanced systemic and/or mucosal response.

An enhanced systemic and/or mucosal immunity is reflected in an enhanced TH1 and/or TH2 immune response. In embodiments, the enhanced immune response includes an increase in the production of IgG1 and/or IgG2a and/or IgA. In embodiments, the mucosal immune response is a TH2 immune response. In one aspect, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. In embodiments, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. In embodiments, the enhanced TH1 immune response will include an increase in IgG2a production.

Immunogenic compositions of the present disclosure, in particular, immunogenic composition comprising one or more antigens of the present disclosure may be used either alone or in combination with other antigens optionally with an immunoregulatory agent capable of eliciting a Th1 and/or Th2 response.

The immunogenic composition of the present disclosure may also comprise one or more immunoregulatory agents, such as a mineral salt, such as an aluminum salt and an oligonucleotide containing a CpG motif. In embodiments, the immunogenic composition includes both an aluminum salt and an oligonucleotide containing a CpG motif. Alternatively, the immunogenic composition includes an ADP ribosylating toxin, such as a detoxified ADP ribosylating toxin and an oligonucleotide containing a CpG motif. In one aspect, the one or more immunoregulatory agents include an adjuvant. The adjuvant may be selected from one or more of the group consisting of a TH1 adjuvant and TH2 adjuvant, further discussed above.

The immunogenic compositions of the present composition may elicit both a cell mediated immune response as well as a humoral immune response in order to effectively address an infection. This immune response may induce long lasting (e.g., neutralizing) antibodies and a cell mediated immunity that may quickly respond upon exposure to one or more infectious antigens. By way of example, evidence of neutralizing antibodies in a subject's blood samples is considered as a surrogate parameter for protection since their formation is of decisive importance for virus elimination in TBE infections.

Use of the Immunogenic Compositions as Medicaments

The instant disclosure also provides a composition for use as a medicament. The medicament may be able to raise an immune response in a mammal (i.e., it is an immunogenic composition) and may be a vaccine. The present disclosure also provides the use of the instant compositions in the manufacture of a medicament for raising an immune response in a mammal. The medicament may be a vaccine. In embodiments, the vaccine is used to prevent and/or treat an intestinal infection such as gastroenteritis, including acute gastroenteritis. The gastroenteritis may result from an imbalance in ion and/or water transfer resulting in both watery diarrhea and/or intestinal peristalisis and/or motility (vomiting).

The instant disclosure provides methods for inducing or increasing an immune response using the compositions described above. The immune response may be protective and may induce antibodies and/or cell-mediated immunity (including systemic and mucosal immunity). Immune responses include booster responses.

The present disclosure also provides a method for raising an immune response in a mammal comprising the step of administering an effective amount of a composition of the instant disclosure. The immune response may be protective and may involve antibodies and/or cell-mediated immunity. In embodiments, the immune response includes one or both of a TH1 immune response and a TH2 immune response. The method may raise a booster response.

Kits

The present disclosure also provides kits comprising one or more containers of compositions as described herein. Compositions may be in liquid form or may be lyophilized, as may individual antigens. Suitable containers for the compositions include, for example, bottles, vials, syringes, and test tubes. Containers may be formed from a variety of materials, including glass or plastic. A container may have a sterile access port (for example, the container may be an intravenous solution bag or a vial having a stopper pierceable by a hypodermic injection needle).

The kit may further comprise a second container comprising a pharmaceutically-acceptable buffer, such as phosphate-buffered saline, Ringer's solution, or dextrose solution. It may also contain other materials useful to the end-user, including other pharmaceutically acceptable formulating solutions such as buffers, diluents, filters, needles, and syringes or other delivery device. The kit may further include a third component comprising an adjuvant.

The kit may also comprise a package insert containing written instructions for methods of inducing immunity or for treating infections. The package insert may be an unapproved draft package insert or may be a package insert approved by the Food and Drug Administration (FDA) or other regulatory body.

In embodiments, a delivery device is pre-filled with the immunogenic compositions as disclosed herein.

Methods of Producing Rotavirus Specific Antibodies

The Rotavirus polypeptides described herein may be used to produce Rotavirus-specific polyclonal and monoclonal antibodies that specifically bind to/are selective for Rotavirus antigens, respectively. Polyclonal antibodies may be produced by administering Rotavirus polypeptides to a mammal, such as a mouse, a rabbit, a goat, or a horse. Serum from the immunized animal is collected and the antibodies are purified from the plasma by, for example, precipitation with ammonium sulfate, followed by chromatography, including affinity chromatography. Techniques for producing and processing polyclonal antisera are known in the art.

Monoclonal antibodies directed against Rotavirus-specific epitopes present in the polypeptides may also be readily produced. Normal B cells from a mammal, such as a mouse, immunized with Rotavirus polypeptides, may be fused with, for example, HAT-sensitive mouse myeloma cells to produce hybridomas. Hybridomas producing Rotavirus-specific antibodies may be identified using RIA or ELISA and isolated by cloning in semi-solid agar or by limiting dilution. Clones producing Rotavirus-specific antibodies are isolated by another round of screening.

Antibodies, i.e., monoclonal and antibodies from polyclonal sera (polyclonal), which are directed against Rotavirus epitopes, are particularly useful for detecting the presence of Rotavirus antigens in a sample, such as a serum sample from a Rotavirus-infected subject. An immunoassay for Rotavirus antigens may utilize one antibody or several antibodies. An immunoassay for Rotavirus antigens may use, for example, a monoclonal antibody directed towards Rotavirus epitopes, a combination of monoclonal antibodies directed towards epitopes of Rotavirus polypeptides, monoclonal antibodies directed towards epitopes of different Rotavirus polypeptides, polyclonal antibodies directed towards the same Rotavirus antigens, polyclonal antibodies directed towards different Rotavirus antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate Rotavirus particles or antigens by immunoaffinity columns. The antibodies may be affixed to a solid support by, for example, adsorption or by covalent linkage so that the antibodies retain their immunoselective activity. Optionally, spacer groups may be included so that the antigen binding site of the antibody remains accessible. The immobilized antibodies may then be used to bind Rotavirus particles or antigens from a biological sample, such as blood or plasma. The bound Rotavirus particles or antigens are recovered from the column matrix by, for example, a change in pH.

All patent literature cited in the instant disclosure is incorporated by reference in their entireties herein.

EXAMPLES

Example 1. Baculovirus Protein Subunit Production

The Recombinant Baculovirus protein expression system was based on nucleic acid sequences for targeted Rotavirus viral proteins (i.e., SEQ ID NOs: 2, 4, 6, 8, 10, 12, 14, 16, 18 and 46). The final sequences were optimized for expression in in-house *Spodoptera frugiperda* insect cells (Sf9) to ensure that appropriate restriction endonuclease sites were present at the termination of the sequences.

A pBacPAK8 cloning vector (Clontech Laboratories, Inc., Mountain View, CA) was used to prepare plasmid vectors containing the target sequences. The plasmid vectors contain flanking sequences homologous to the linear BestBac 2.0 Baculovirus vector (Expression Systems, Davis, CA), such that when the plasmid containing the various VP4/VP7 inserts were co-transfected into Sf9 cells with the linear BestBac 2.0 virus Baculovirus backbone (Expression Systems, Davis, CA), homologous recombination exchanges the insert for the polyhedrin gene of the Baculovirus. The resulting Baculovirus containing the Rotavirus viral sequences expressed under control of the polyhedrin promoter were then harvested. Cells and virus were grown in culture media obtained from Expression Systems (Davis, CA, Media ES 99-300) formulated without animal origin ingredients. Gentamicin solution is added to a final concentration of 10 μg/ml from purchased stock solution (Thermo Fisher Scientific, Waltham, MA, Gibco Cat #15710). At final harvest, infected cultures were centrifuged to remove the cells and the supernatants collected. The supernatants were processed through 0.2-micron sterile disposable filter. The premaster cultures were titered to determine final concentrations.

Sf9 cells was scaled up to production quantities utilizing glass or sterile disposable plastic vessel volumes. Upon reaching the final cell culture volume required for production, virus infection occurs in the same vessel as the final passage of cells. Culture mixing was achieved through shaking/rocking of the container or utilizing low shear type impeller design. Mixing speed and intensity was adjusted to maintain cells in suspension without creating excess shear or foaming which will cause cell disruption.

Viral fluids were inactivated with beta-propiolactone (BPL) at a final concentration of 0.2-0.3%. Prior to inactivation, the pH of the disrupted fluids were adjusted to 7.5-8.0 using 2-ION NaOH as base or 10-38% HCl or 10% nitric acid as acid. The disrupted fluids were allowed to warm to room temperature for 1-18 hours prior to the addition of BPL. BPL was added at the concentration specified above, with mixing. After the addition of BPL, the viral fluids were transferred to an inactivation container utilizing a "bottom to bottom" transfer process to ensure that all fluids come into contact with BPL. The disrupted fluids were incubated at 17-27° C. for 18-48 hours with agitation. After the inactivation process was complete, the pH was adjusted to 7.0-7.5 with acid or base as mentioned above. The inactivated virus fluids were stored at 2-8° C. until further processing. The antigens were prepared with Water/Oil/Water (WOW) adjuvants.

Example 2. Evaluation of Rotavirus Antigens Based Vaccine in Mice

Experimental prescription platform vaccines were produced according to the above outline of production containing either one or two relevant proteins from each isolate (encoding SEQ ID NO:18, VP7 RVA and SEQ ID NO:46, VP4 RVA).

Mice were vaccinated twice at 3-week intervals with an appropriately reduced dose of the swine vaccine, and serum harvested 28-35 days post second vaccination. Sera was then tested in standard virus neutralization assays using either homologous or heterologous Rotavirus isolates. In addition, viral sequences corresponding to the native virus, or the adapted sequence used in recombinant baculovirus were analyzed for predicted secondary structure and immune epitopes. In a final series of experiments, test vaccines used in mouse studies were administered to feeder pigs, and sera collected for analysis of cross-neutralization with homologous and heterologous virus.

A field isolate was identified and successfully cultured (termed Rotavirus A1). Based upon viral sequences derived from the genome, baculoviruses were produced independently, each of which expressed a single target viral protein from the homologous virus Rotavirus A1. These proteins were prepared according to the above and formulated either individually or in combination vaccine products that were then administered to separate groups of mice. Serum harvested from these mice was then tested for neutralization of homologous virus, and the results presented in Table 1.

TABLE 1

Serum neutralization titers to Rotavirus A1 following vaccination with various protein targets.

| Protein Target | SN Titer |
|---|---|
| VP4 | 1280 |
| | 160 |

TABLE 1-continued

Serum neutralization titers to Rotavirus A1 following vaccination with various protein targets.

| Protein Target | SN Titer |
|---|---|
| VP7 | 40 |
| | 40 |
| VP4 + VP7 | 1280 |
| | 640 |
| VP4 + VP6 + VP7 | 320 |
| No vaccine | <20 |

Example 3. Cross-Neutralization of Mouse Sera Against Homologous and Heterologous Virus Based upon the results obtained in Example 2, a second study was carried-out to examine the relative importance of sequence conservation of the target proteins in providing protection in mice to either heterologous or homologous virus. Briefly, mice were vaccinated with each of two proteins individually or with a combination of both proteins, and the result sera analyzed for cross-neutralization. The original virus designation, as well as the recombinant baculovirus construct designation are presented in Table 2 for one experiment.

TABLE 2

Protein Sequence Homology between the native viral protein and test baculovirus.

| Baculovirus | Rotavirus Isolate | | | | | |
|---|---|---|---|---|---|---|
| Subunit Protein | 6-091920 | 3-080820 | 1-073020 | 8-100620 | 7-100620 | 4-090920 |
| SEQ ID NO: 46 | 82.3% | 82.0% | 77.9% | 82.8% | 82.3% | 77.8% |
| SEQ ID NO: 2 | 78.8% | 78.5% | 95.4% | 81.9% | N/A | NA |

Based upon the serological results obtained in vitro, the relative importance of each protein and the importance of sequence homology to the target virus was compared, with the results expressed in Table 3.

TABLE 3

Serum neutralization titers following vaccination with either a combination or single-protein vaccine.

| Vaccine | Rotavirus Isolate | | | | | |
|---|---|---|---|---|---|---|
| Subunit Protein | 6-091920 | 3-080820 | 1-073020 | 8-100620 | 7-100620 | 4-090920 |
| SEQ ID NOs: 46 and 2 | Neg | Neg | 1:525 | Neg | 1:390 | 1:431 |
| SEQ ID NO: 46 | Neg | Neg | 1:593 | Neg | 1:403 | 1:403 |
| SEQ ID NO: 2 | Neg | Neg | 1:80 | Neg | Neg | Neg |
| Sham | Neg | Neg | 1:48 | Neg | Neg | Neg |

It was evident that one of the two selected viral proteins appeared to provide the majority of protection observed, and that the sequence homology between the target viral protein and the vaccine construct was not highly predictable.

Example 3. Field Evaluation of Rotavirus Antigens Based Vaccine

The vaccine study was designed to incorporate general field evaluation to demonstrate Rotavirus A & C vaccine reduction in clinical signs of infection. The primary outcome being to increase economical swine production by decreasing Rotavirus A & C impact.

Four thousand (4000) doses was considered the minimum number of doses deemed necessary to accurately evaluate if the vaccine is reducing the incidence of Rotavirus. The Rotavirus antigens were manufactured as described above with the Rotavirus A & C genes of interest included (SEQ ID NOs: 1, 3, 5, 7, 9, 11, 13, 15, and 17) to form the combination-antigen vaccine (MEDGENE™'s/Applicants' vaccine). A 21-day withdrawal period before slaughter was used.

TABLE 4

Trial Background Data.

| | |
|---|---|
| Species/Breed/Strain | Porcine Line 03 |
| Sex | Mixed |
| Age at Day 0 | At least 21 days of age |
| Number of Doses Used | 4000 |
| Housing | Pigs were housed according to farm standards (SOPs) |
| Feed and Water | Animals were fed age-appropriate feed according to SOPs. Water was available ad libitum. |
| Vaccination | All sows and gilts received the same vaccine, given as a 2 mL intramuscular dose. Vaccine was used according to label instructions, under the direction of the veterinarian. |
| Summary and Analysis | Performance parameters were recorded weekly.<br>Evaluation was at 16 weeks. |
| Parameters | Success is litters treated/week reduced from 10-20 to <10 litters/week. Success is an improvement in pre-wean mortality from 20% to <15%. |
| Farrowing Piglet Diagnostic Workup | (i) Executed when observes three consecutive weeks of litter diarrhea incidence in the vaccination time-period that is greater than the baseline litter diarrhea incidence.<br>(ii) Executed at discretion.<br>(iii)Tissue submissions for pathology was defined as 3-5 piglets with clinical diarrhea. The enteric workup objective was to determine diarrhea etiology. |

The Trial started with breeding group 10 and data was collected past breeding group 21. Each sow's litter's score was based on a score card (not shown). The scores were as follows:

- Score 0
  - Clean dry pigs
  - No loose stools
- Score 1
  - Majority of litter at Score 0
  - 1-2 with loose stool
- Score 2
  - Less than about half of litter with loose stools
- Score 3
  - Half of litter with loose stool
  - Evidence of loose stool on all pigs
  - Predominantly dry
  - Few to most pigs with red anus and visibly wet
- Score 4
  - More than half of litter with loose stool
- Score 5
  - Entire litter with loose stool
  - Wet and chilled pigs
  - Loss in body condition Scores were collected 4 days post farrowing. Groups 10-15 & 18 were mixed groups, Groups 16-17 were all competitor (SEQUIVITY™, Merck Animal Health, Rahway, NJ; "RNA-based vaccine") vaccine, Groups 19-21 were all MEDGENE™ (Applicants') vaccine.

TABLE 5

Trial Parity Results.

| | |
|---|---|
| Breeding Groups | 4 |
| Sows on Trial | 1109<br>MEDGENE ™ Vaccine - 565<br>RNA-based Vaccine - 544 |
| Parity* Breakdown | MEDGENE ™ Vaccine<br>P1 - 173<br>P2 - 64<br>P3 - 89<br>P4 - 78<br>P5+ - 166<br>RNA-based Vaccine<br>P1 - 106<br>P2 - 87<br>P3 - 99<br>P4 - 81<br>P5+ - 166 |

*Parity - is a swine age/reproduction measurement. P1 - the female has given birth (farrowed) to her first litter of pigs, Parity 2 - female has farrowed her 2nd litter of pigs, P3 - third and so on.

MEDGENE™ vaccine contained a combination of peptides as set forth in SEQ ID NOs: 2 (VP7 RVA), 4 (VP4 RVA), 6 (VP4 RVA), 8 (VP7 RVC), 10 (VP4 RVC), 12 (VP4 RVA), 14 (VP4 RVC), 16 (VP7 RVC) and 18 (VP7 RVC).

Figure 1B:
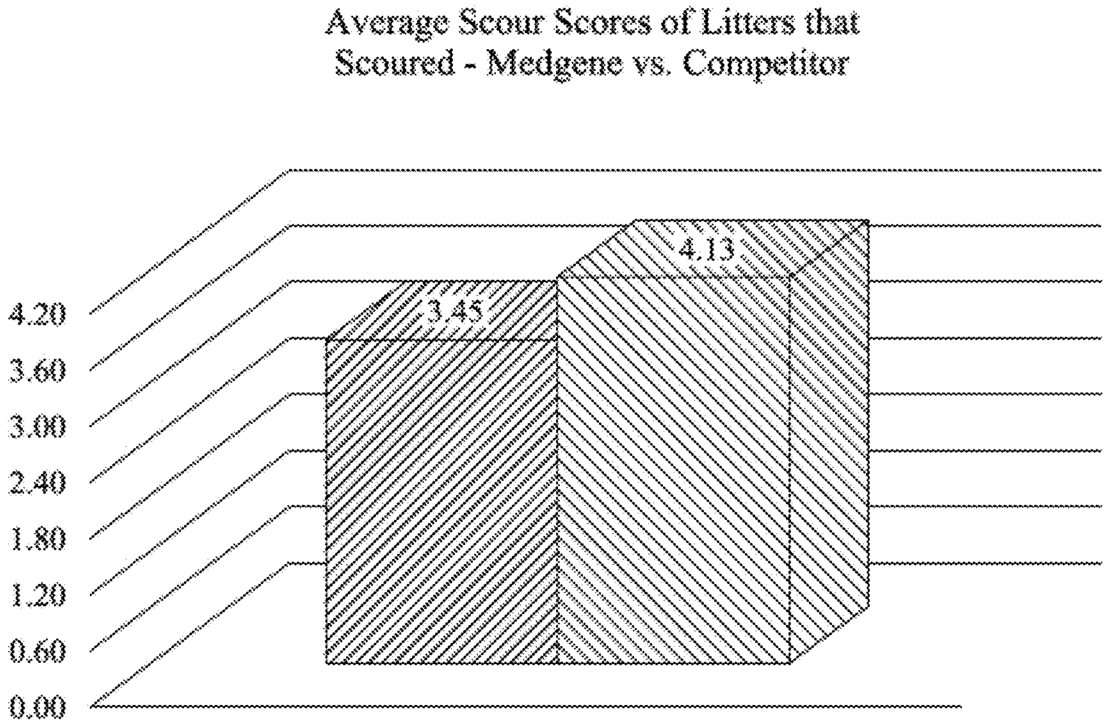
Figure 2A:
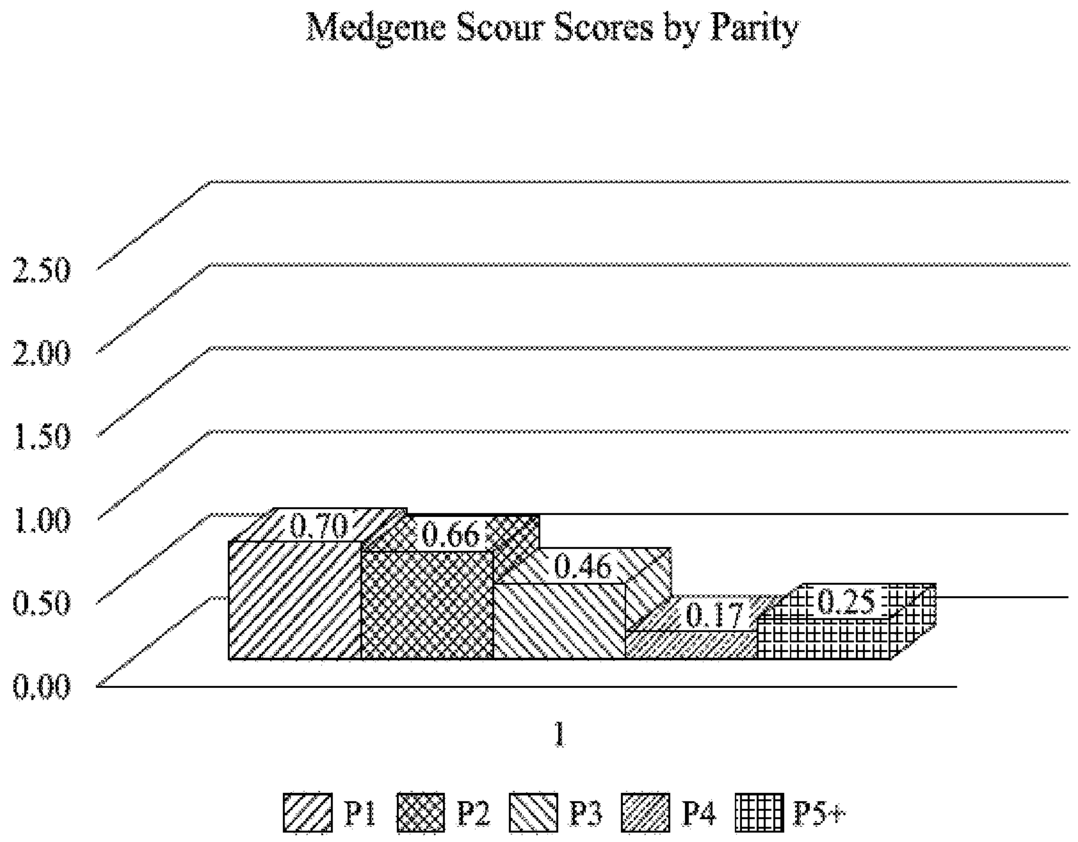
FIGS. 2 *a, b* illustrate the Parity results from the vaccination between MEDGENE™'s (Applicants') vaccine and an RNA-based vaccine in swine.
Figure 2B:
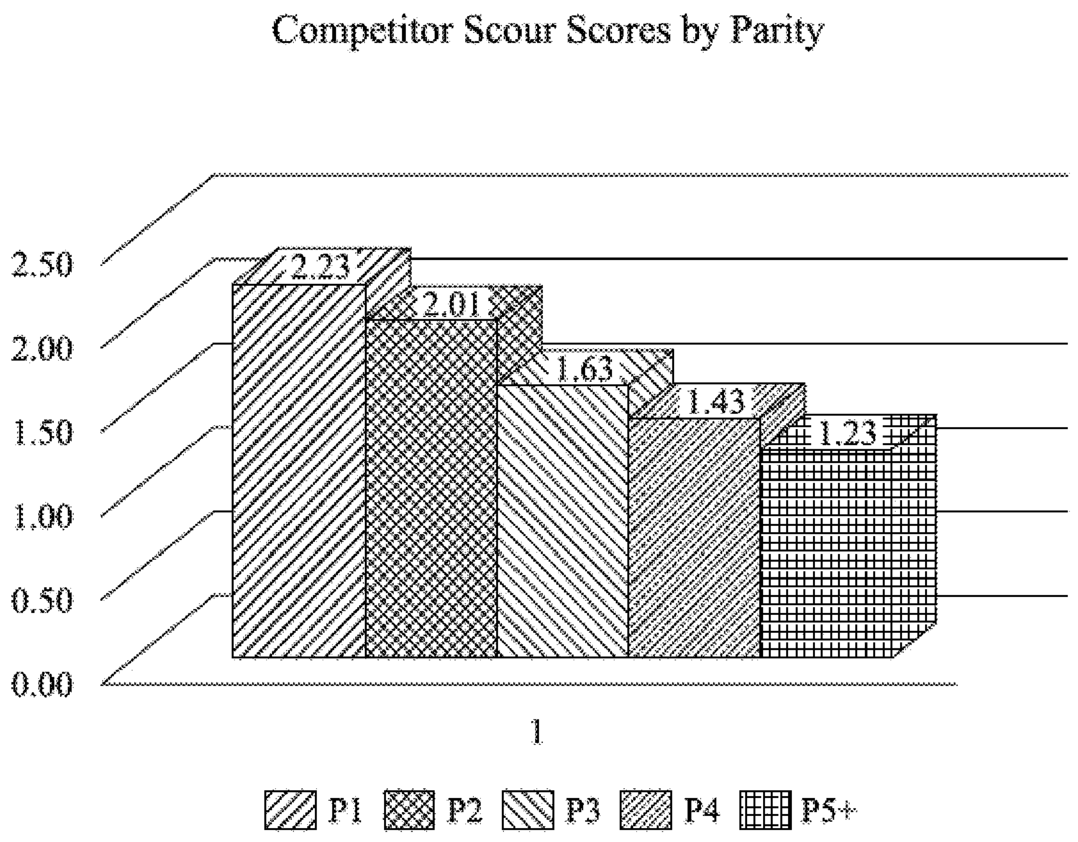

FIGS. 1 and 2 show the results of the trials. As may be seen in FIG. 1, the MEDGENE™ vaccine has lower scores, and thus, is more effective than the RNA-based vaccine. Further, from FIG. 2, it may be seen that (though not statistically significant) there is a more positive trend for Parity for the MEDGENE™ vaccine vs. the RNA-based vaccine.

Although the invention has been described with reference to the above examples, it will be understood that modifications and variations are encompassed within the spirit and scope of the invention. Accordingly, the invention is limited only by the following claims.

The sequence listing submitted on 2024 Mar. 1 has the file name "Rotavirus.xml", was created on 2024 Mar. 1, and has a file size of 81 KB, which sequence listing is incorporated herein by reference.

I claim herein:

1. A method for producing a composition comprising Rotavirus-derived immunogenic polypeptides and/or peptides, wherein said immunogenic polypeptides and/or peptides are mixed or co-expressed with one or more adjuvants, and wherein the polypeptides and/or peptides comprise the amino acid sequences as set forth in SEQ ID NOs: 2, 4, 6, 8, 10, 12, 14, 16 and 18.

2. An immunogenic composition comprising the polypeptides as set forth in SEQ ID NOs: 2, 4, 6, 8, 10, 12, 14, 16 and 18, wherein said polypeptides are mixed or co-expressed with one or more adjuvants.

3. A method of eliciting an immunological response in a subject comprising administering a composition as set forth in claim 2.

4. The method of claim 3, further comprising administering an adjuvant.

5. The method of claim 4, wherein administering said immunogenic composition to said subject is via intramuscular administration.

6. The method of claim 3, wherein said administration is by multiple administrations.

7. A composition comprising the combination of polypeptides as set forth in SEQ ID NOs: 2, 4, 6, 8, 10, 12, 14, 16 and 18.

8. The composition of claim 7, where said composition is formulated as a vaccine.

9. The composition of claim 8, wherein the composition further comprises an adjuvant.

10. The composition of claim 9, wherein the adjuvant is a water/oil/water adjuvant.

11. The composition of claim 7, wherein the composition elicits neutralizing antibodies at a single dose.

* * * * *

SEQUENCE LISTING

```
Sequence total quantity: 52
SEQ ID NO: 1          moltype = DNA  length = 1058
```

```
FEATURE                Location/Qualifiers
source                 1..1058
                       mol_type = other DNA
                       organism = Rotavirus A
SEQUENCE: 1
accgagctcg aattcatgta tggaatcgaa tacacaaccg tccttacctt ccttatatct  60
ataatccttc tcaattatat attgaagtct ctgacgagca ccatggattt tatcatctac  120
agattcctcc tgcttattgc gatagtgagt ccatttgtta agacgcaaaa ttacggaatc  180
aacctcccaa taacaggctc tatggatacg gcatacgcaa actcatcaca acaagaaacg  240
tttcttactt ctacattgtg cctttactac ccgactgagg ctagcactca gattggcgat  300
gctgagtgga agaacacact ttcccaactc tttctcacta aaggctggcc gactggttcg  360
gtatatttta aggagtacac aaatatcgct tccttttcca tcgatccaca actgtactgc  420
gattacaacg tagttttgat gaaatatgac tcaaccctgg aattggacat gtcggagctt  480
gcggacctta ttctcaacga gtggctgtgt aatccgatgg acatcacatt gtactattat  540
cagcagacgg acgaagcgaa caaatggatt agcatgggtc agtcttgcac tgttaaagtt  600
tgcccactca atacacaaac tctgggcata ggatgcacca ctacaaatac tgcgacgttc  660
gaagaagtag caagagatga aaaattggta atcaccgatg tcgtcgatgg agtcaaccat  720
aaactggacg ttactaccaa tacatgtacg ataagaaatt gcaaaaaatt gggaccgaga  780
gaaaatgttg ccataataca agttggtggt agtgaggtcc ttgatgttac tgctgacccc  840
actaccgctc cgcagacaga gcgcatgatg agggtaaact ggaagaaatg gtggcaagtt  900
ttttatactg tcgtagatta cataaaccag atcgtccaag tcatgagtaa aagatctcgt  960
tcactgaact ctgccgcgtt ttattatagg gtgaagggcg aaaacttgta ctttcaaggc  1020
catcaccatc accatcacta ggcggccgct taattaat                         1058

SEQ ID NO: 2           moltype = AA  length = 1023
FEATURE                Location/Qualifiers
source                 1..1023
                       mol_type = protein
                       organism = Rotavirus A
SEQUENCE: 2
METTYRGLYI LEGLUTYRTH RTHRVALLEU THRPHELEUI LESERILEIL ELEULEUASN  60
TYRILELEUL YSSERLEUTH RSERTHRMET ASPPHEILEI LETYRARGPH ELEULEULEU  120
ILEALAILEV ALSERPROPH EVALLYSTHR GLNASNTYRG LYILEASNLE UPROILETHR  180
GLYSERMETA SPTHRALATY RALAASNSER SERGLNGLNG LUTHRPHELE UTHRSERTHR  240
LEUCYSLEUT YRTYRPROTH RGLUALASER THRGLNILEG LYASPALAGL UTRPLYSASN  300
THRLEUSERG LNLEUPHELE UTHRLYSGLY TRPPROTHRG LYSERVALTY RPHELYSGLU  360
TYRTHRASNI LEALASERPH ESERILEASP PROGLNLEUT YRCYSASPTY RASNVALVAL  420
LEUMETLYST YRASPSERTH RLEUGLULEU ASPMETSERG LULEUALAAS PLEUILELEU  480
ASNGLUTRPL EUCYSASNPR OMETASPILE THRLEUTYRT YRTYRGLNGL NTHRASPGLU  540
ALAASNLYST RPILESERME TGLYGLNSER CYSTHRVALL YSVALCYSPR OLEUASNTHR  600
GLNTHRLEUG LYILEGLYCY STHRTHRTHR ASNTHRALAT HRPHEGLUGL UVALALAARG  660
ASPGLULYSL EUVALILETH RASPVALVAL ASPGLYVALA SNHISLYSLE UASPVALTHR  720
THRASNTHRC YSTHRILEAR GASNCYSLYS LYSLEUGLYP ROARGGLUAS NVALALAILE  780
ILEGLNVALG LYGLYSERGL UVALLEUASP VALTHRALAA SPPROTHRTH RALAPROGLN  840
THRGLUARGM ETMETARGVA LASNTRPLYS LYSTRPTRPG LNVALPHETY RTHRVALVAL  900
ASPTYRILEA SNGLNILEVA LGLNVALMET SERLYSARGS ERARGSERLE UASNSERALA  960
ALAPHETYRT YRARGVALLY SGLYGLUASN LEUTYRPHEG LNGLYHISHI SHISHISHIS  1020
HIS                                                               1023

SEQ ID NO: 3           moltype = DNA  length = 2408
FEATURE                Location/Qualifiers
source                 1..2408
                       mol_type = other DNA
                       organism = Rotavirus A
SEQUENCE: 3
accgagctcg aattcatggc gagcttgatt taccgacaat tacttacgaa ctcctacact  60
gtggatctgt cggacgaaat tcagattatt gggagcgaga aggcccaaaa tgtgaccatc  120
aatccggggc catttgctca aactgggtat gcacccgtta actggggacc aggtgagacc  180
aatgatagta cgaccgtaga gccggtgctt gacggaccct atcagccgac cacgtttaac  240
cctcctgtaa gctattggat cctcttatca ccgtcgaacg ctggcgtcgt cgtagagggt  300
acaaacaact cagatagatg gctcgcaacc attttaatcg agccaaatgt gacttctgag  360
tcgcgcacat atacactctt cggccgccaa gagcagatca ccgtggagaa tgtcagtacc  420
acgaagtgga aatttgtaga cctcgcgaag accgacataa atggaacgtt cactcaacac  480
gggccactgc tctcggatac taagctttac ggggttatga agttttctgg cagattgtac  540
acgtataatg gagagactcc caacgccact accggttatt acaccaccac caactacgat  600
actgtaaata tgacatcaca ttgcgatttc tacatcatcc cccgtagtga agagaatgcc  660
tgtacaaact acataaataa tggtctacca ccgatccaga ataccagaaa cgtcgttcca  720
gttagcctca cttctcgctc tattgtacat acacgagcac aggcaaacga ggacattgtg  780
gttagtaaaa ccagcctgtg gaaagaaatg cagtataacc gcgatattac gatccgtttc  840
aagttcgcta acgctattat taagagtgga ggcctggggt acaagtggtc tgagataagt  900
tttaagccag ccaactacca gtacaactac acccgtgatg gtgaggttat aactgcccat  960
acgacctgct cggtaaatgg gataaacgac ttcagttaca acggcggtag cctacctacg  1020
gattttgtaa ttagtagata cgaggtcatt aaggagaaca gttacgtgta cgtagactac  1080
tgggatgaca gccaagcatt ccgcaacatg gtctatgtgc gtagtcttgc ggcgaatcta  1140
aactcagtga cctgtactgg cggaaactat gactttcgtc ttccggtggg ggcttggcca  1200
gtaatgactg gaggggcggt cagtctacgc cctgctgggg tcacactgag cactcaattt  1260
acggattttg tatcactaaa cagcctacga tttaggttct ccctgtctgt agaggagccg  1320
ccctttgcaa tagcccgaac gcgagttagc ggactctacg ggctccctgc tgccaaccct  1380
aataacggta aggactacta tgagattctg ggtaggtttt ccctaatctc actagttcct  1440
```

```
agtaacgacg actatcagac cccgataatg aacagcgtca ccgtgaggca ggatttagaa  1500
agacaactca acgaacttcg acaggagttc aattctctga gtcaagaaat agcgatgagt  1560
cagttgatag atctggcact gctaccattg gatatgttct caatgttttc tgggataaag  1620
tcgacaatag atgcggcgaa aagcatggcg acctcggtta tgaagaagtt caagcgcagt  1680
aatctagcta gcagcatttc gacgcttact gactcactaa gcgacgcagc ctcttcgatc  1740
tcacgtaacc catccatacg cagcgtcgga tcctcagtca gtgtgtggac ggacatctcc  1800
acacaggcga ctgatattag tgataccttt aaatcagtga gtacccaaac gtcgacaatt  1860
tcaagaagat tacgacttaa ggaaattact acccaaacag aaggtatgaa ttttgatgat  1920
atcagcgcgg cagtactgaa aaccaaaatc gataaatctg ttcaaatctc accaaacaca  1980
ctacccgaca tcgttacaga agcaagtgaa aagttcatcc ctaatcgtac ataccgtgta  2040
attaaagatg acgaggttct ggaggctggg actgacggac gtttcttcgc ctataaagta  2100
gatacctttg acgaaatacc tttcgatgtc cagaagtttg cagatcttgt gacggatagt  2160
cctgtcataa gtgcaatcat agattttaaa acattgaaaa atctgaatga caactatggc  2220
atcacaaggg aacaagcctt taatctgttg agatccgacc caagggtgct aagggagttc  2280
atcaatcaag aaaatccgat aatacgtaat cgcattgaac agcttatact acaatgtaga  2340
cttaagggcg aaaacttgta ctttcaaggc catcaccatc accatcacta ggcggccgct  2400
taattaat                                                           2408

SEQ ID NO: 4           moltype = AA  length = 2373
FEATURE                Location/Qualifiers
source                 1..2373
                       mol_type = protein
                       organism = Rotavirus A
SEQUENCE: 4
METALASERL EUILETYRAR GGLNLEULEU THRASNSERT YRTHRVALAS PLEUSERASP  60
GLUILEGLNI LEILEGLYSE RGLULYSALA GLNASNVALT HRILEASNPR OGLYPROPHE  120
ALAGLNTHRG LYTYRALAPR OVALASNTRP GLYPROGLYG LUTHRASNAS PSERTHRTHR  180
VALGLUPROV ALLEUASPGL YPROTYRGLN PROTHRTHRP HEASNPROPR OVALSERTYR  240
TRPILELEUL EUSERPROSE RASNALAGLY VALVALVALG LUGLYTHRAS NASNSERASP  300
ARGTRPLEUA LATHRILELE UILEGLUPRO ASNVALTHRS ERGLUSERAR GTHRTYRTHR  360
LEUPHEGLYA RGGLNGLUGL NILETHRVAL GLUASNVALS ERTHRTHRLY STRPLYSPHE  420
VALASPLEUA LALYSTHRAS PILEASNGLY THRPHETHRG LNHISGLYPR OLEULEUSER  480
ASPTHRLYSL EUTYRGLYVA LMETLYSPHE SERGLYARGL EUTYRTHRTY RASNGLYGLU  540
THRPROASNA LATHRTHRGL YTYRTYRTHR THRTHRASNT YRASPTHRVA LASNMETTHR  600
SERHISCYSA SPPHETYRIL EILEPROARG SERGLUGLUA SNALACYSTH RASNTYRILE  660
ASNASNGLYL EUPROPROIL EGLNASNTHR ARGASNVALV ALPROVALSE RLEUTHRSER  720
ARGSERILEV ALHISTHRAR GALAGLNALA ASNGLUASPI LEVALVALSE RLYSTHRSER  780
LEUTRPLYSG LUMETGLNTY RASNARGASP ILETHRILEA RGPHELYSPH EALAASNALA  840
ILEILELYSS ERGLYGLYLE UGLYTYRLYS TRPSERGLUI LESERPHELY SPROALAASN  900
TYRGLNTYRA SNTYRTHRAR GASPGLYGLU VALILETHRA LAHISTHRTH RCYSSERVAL  960
ASNGLYILEA SNASPPHESE RTYRASNGLY GLYSERLEUP ROTHRASPPH EVALILESER  1020
ARGTYRGLUV ALILELYSGL UASNSERTYR VALTYRVALA SPTYRTRPAS PASPSERGLN  1080
ALAPHEARGA SNMETVALTY RVALARGSER LEUALAALAA SNLEUASNSE RVALTHRCYS  1140
THRGLYGLYA SNTYRASPPH EARGLEUPRO VALGLYALAT RPPROVALME TTHRGLYGLY  1200
ALAVALSERL EUARGPROAL AGLYVALTHR LEUSERTHRG LNPHETHRAS PPHEVALSER  1260
LEUASNSERL EUARGPHEAR GPHESERLEU SERVALGLUG LUPROPROPH EALAILEALA  1320
ARGTHRARGV ALSERGLYLE UTYRGLYLEU PROALAALAA SNPROASNAS NGLYLYSASP  1380
TYRTYRGLUI LELEUGLYAR GPHESERLEU ILESERLEUV ALPROSERAS NASPASPTYR  1440
GLNTHRPROI LEMETASNSE RVALTHRVAL ARGGLNASPL EUGLUARGGL NLEUASNGLU  1500
LEUARGGLNG LUPHEASNSE RLEUSERGLN GLUILEALAM ETSERGLNLE UILEASPLEU  1560
ALALEULEUP ROLEUASPME TPHESERMET PHESERGLYI LELYSSERTH RILEASPALA  1620
ALALYSSERM ETALATHRSE RVALMETLYS LYSPHELYSA RGSERASNLE UALASERSER  1680
ILESERTHRL EUTHRASPSE RLEUSERASP ALAALASERS ERILESERAR GASNPROSER  1740
ILEARGSERV ALGLYSERSE RVALSERVAL TRPTHRASPI LESERTHRGL NALATHRASP  1800
ILESERASPT HRPHELYSSE RVALSERTHR GLNTHRSERT HRILESERAR GARGLEUARG  1860
LEULYSGLUI LETHRTHRGL NTHRGLUGLY METASNPHEA SPASPILESE RALAALAVAL  1920
LEULYSTHRL YSILEASPLY SSERVALGLN ILESERPROA SNTHRLEUPR OASPILEVAL  1980
THRGLUALAS ERGLULYSPH EILEPROASN ARGTHRTYRA RGVALILELY SASPASPGLU  2040
VALLEUGLUA LAGLYTHRAS PGLYARGPHE PHEALATYRL YSVALASPTH RPHEASPGLU  2100
ILEPROPHEA SPVALGLNLY SPHEALAASP LEUVALTHRA SPSERPROVA LILESERALA  2160
ILEILEASPP HELYSTHRLE ULYSASNLEU ASNASPASNT YRGLYILETH RARGGLUGLN  2220
ALAPHEASNL EULEUARGSE RASPPROARG VALLEUARGG LUPHEILEAS NGLNGLUASN  2280
PROILEILEA RGASNARGIL EGLUGLNLEU ILELEUGLNC YSARGLEULY SGLYGLUASN  2340
LEUTYRPHEG LNGLYHISHI SHISHISHIS HIS                               2373

SEQ ID NO: 5           moltype = DNA  length = 1076
FEATURE                Location/Qualifiers
source                 1..1076
                       mol_type = other DNA
                       organism = Rotavirus A
SEQUENCE: 5
accgagctcg aattcatggt ttgcaccacc ctctacacgg tctgcgtgat cctgtgtatt  60
ctcttcattt acatgttgct tttccgtaag atgttccacc tcattacgga taccgtaata  120
gtagcgataa taatctccaa ttgtgttggc tggactcaag gtcaaatgtt catcgacaat  180
atgcattacg aaggaaatat cgagacgatt atcaatgcta cgaatccatt taacgtagaa  240
agtctttgca tatatttccc aaaagcggtg gttggaagtc agggacccgg ccaaatcaac  300
ggatacctga acgacggaaa ctacgcccaa accatagcta cactgttcga gactaagggc  360
ttccctaagg gaagtgtggt gctgaagact tacgcaaaga caagtgactt tatctcttcg  420
gtagagatga cgtgttcgta taacatagtc atcatcccgg atgatccgga taagtctgag  480
```

-continued gcaatcgaac agatagcaga gtggatattg aatgtatgga agtgtgatga tatggatctt 540
aacatataca cgtacgaaca aataggaata gacaaccttt gggctgcatt tggcgacgac 600
tgtgacatta gcgtttgccc gctcgatacg accatgaatg gcataggatg ccttccggcg 660
agtacagaaa cgtacgaggt ggtatccaac aacaccgagt tggccctgat taatgtcgta 720
gataacgtaa aacataggat acagatgaac acaggcagat gcaaacttaa aaattgcgtc 780
aagggtgagg cacgcctgaa cacggctata atccgcatat ccaagtctag tagtttcgac 840
aatagtctca gtccaatgaa caacggacag actacgagat cgttcaaaat caacgccaaa 900
aaatggtgga cgatcttcta tacaatcatc gactatatta atacgattgt acaaacgatg 960
acaccgaggc atcgcgccat ttatccagag ggttggatgc tccgctatgc gaagggcgaa 1020
aacttgtact ttcaaggcca tcaccatcac catcactagg cggccgctta attaat 1076

SEQ ID NO: 6 moltype = AA length = 1041
FEATURE Location/Qualifiers
source 1..1041
mol_type = protein
organism = Rotavirus A
SEQUENCE: 6
METVALCYST HRTHRLEUTY RTHRVALCYS VALILELEUC YSILELEUPH EILETYRMET 60
LEULEUPHEA RGLYSMETPH EHISLEUILE THRASPTHRV ALILEVALAL AILEILEILE 120
SERASNCYSV ALGLYTRPTH RGLNGLYGLN METPHEILEA SPASNMETHI STYRGLUGLY 180
ASNILEGLUT HRILEILEAS NALATHRASN PROPHEASNV ALGLUSERLE UCYSILETYR 240
PHEPROLYSA LAVALVALGL YSERGLNGLY PROGLYGLNI LEASNGLYTY RLEUASNASP 300
GLYASNTYRA LAGLNTHRIL EALATHRLEU PHEGLUTHRL YSGLYPHEPR OLYSGLYSER 360
VALVALLEUL YSTHRTYRAL ALYSTHRSER ASPPHEILES ERSERVALGL UMETTHRCYS 420
SERTYRASNI LEVALILEIL EPROASPASP PROASPLYSS ERGLUALAIL EGLUGLNILE 480
ALAGLUTRPI LELEUASNVA LTRPLYSCYS ASPASPMETA SPLEUASNIL ETYRTHRTYR 540
GLUGLNILEG LYILEASPAS NLEUTRPALA ALAPHEGLYA SPASPCYSAS PILESERVAL 600
CYSPROLEUA SPTHRTHRME TASNGLYILE GLYCYSLEUP ROALASERTH RGLUTHRTYR 660
GLUVALVALS ERASNASNTH RGLULEUALA LEUILEASNV ALVALASPAS NVALLYSHIS 720
ARGILEGLNM ETASNTHRGL YARGCYSLYS LEULYSASNC YSVALLYSGL YGLUALAARG 780
LEUASNTHRA LAILEILEAR GILESERLYS SERSERSERP HEASPASNSE RLEUSERPRO 840
METASNASNG LYGLNTHRTH RARGSERPHE LYSILEASNA LALYSLYSTR PTRPTHRILE 900
PHETYRTHRI LEILEASPTY RILEASNTHR ILEVALGLNT HRMETTHRPR OARGHISARG 960
ALAILETYRP ROGLUGLYTR PMETLEUARG TYRALALYSG LYGLUASNLE UTYRPHEGLN 1020
GLYHISHISH ISHISHISHI S 1041

SEQ ID NO: 7 moltype = DNA length = 1076
FEATURE Location/Qualifiers
source 1..1076
mol_type = other DNA
organism = Rotavirus C
SEQUENCE: 7
accgagctcg aattcatggt gtgtacaacc ctgtatacgg tttgcgttat tttgtgcatt 60
ttgttcattt acatgctttt gttccgcaaa atgttccacc tcatcacgga tgctacaatc 120
ataacccttg tgatatctaa ttgtattgga tggtcacaag gtcagatgtt tacagacgac 180
atctattaca acggaaacgt cgaaactgtg gtgaactcga ctgatccatt tgacgtgaga 240
agtctttgca tttactttcc taacgccgtc gtcggatcgc agggacctgg aaaaactgat 300
ggatacctca acgatggtaa ttatgcccag actattgccg cactcttcga aacgaagggt 360
tttccccgtg gatcgatcgt tctcaagaca tatacgaaag tctcagactt cataaattcg 420
gtggaaatga cgtgctcgta taacatcgta attataccgg actcgttgac caacagcgaa 480
tcaatcgaga ggattgcaga gtggatcctt aatgtttggc gttgtgacga catgaatctt 540
gatatctaca catacgaaca gacaggtatc gacaacttgt gggctgcgtt cggtagcgac 600
tgcgacatca gcgtatgtcc gttggacaca accatgaacg gcatcggctg tagtccagca 660
tcaacagaaa cgtatgaagt gctttccaac gatactcagc tcgccctgct taacgttgtg 720
gacaacatta aacatcgcat tcagatgaat accgcaactt gtaaacttaa aaactgcatc 780
aaaggagaag ccagacttaa taccgcgctg attagaatct caacatccag ctccttcgac 840
aactcgctga gcccgctcaa tgacggccaa acaacaaggt cttttaagat aaacgcgaag 900
aagtggtgga cgattttcta cacgatcata gactacatca ataccatagt acagactatg 960
gcgcccagac acagagcgat atatcctgag ggttggatgc tgcgttatgc gaagggcgaa 1020
aacttgtact ttcaaggcca tcaccatcac catcactagg cggccgctta attaat 1076

SEQ ID NO: 8 moltype = AA length = 1041
FEATURE Location/Qualifiers
source 1..1041
mol_type = protein
organism = Rotavirus C
SEQUENCE: 8
METVALCYST HRTHRLEUTY RTHRVALCYS VALILELEUC YSILELEUPH EILETYRMET 60
LEULEUPHEA RGLYSMETPH EHISLEUILE THRASPALAT HRILEILETH RLEUVALILE 120
SERASNCYSI LEGLYTRPSE RGLNGLYGLN METPHETHRA SPASPILETY RTYRASNGLY 180
ASNVALGLUT HRVALVALAS NSERTHRASP PROPHEASPV ALARGSERLE UCYSILETYR 240
PHEPROASNA LAVALVALGL YSERGLNGLY PROGLYLYST HRASPGLYTY RLEUASNASP 300
GLYASNTYRA LAGLNTHRIL EALAALALEU PHEGLUTHRL YSGLYPHEPR OARGGLYSER 360
ILEVALLEUL YSTHRTYRTH RLYSVALSER ASPPHEILEA SNSERVALGL UMETTHRCYS 420
SERTYRASNI LEVALILEIL EPROASPSER LEUTHRASNS ERGLUSERIL EGLUARGILE 480
ALAGLUTRPI LELEUASNVA LTRPARGCYS ASPASPMETA SNLEUASPIL ETYRTHRTYR 540
GLUGLNTHRG LYILEASPAS NLEUTRPALA ALAPHEGLYS ERASPCYSAS PILESERVAL 600
CYSPROLEUA SPTHRTHRME TASNGLYILE GLYCYSSERP ROALASERTH RGLUTHRTYR 660
GLUVALLEUS ERASNASPTH RGLNLEUALA LEULEUASNV ALVALASPAS NILELYSHIS 720

```
ARGILEGLNM ETASNTHRAL ATHRCYSLYS LEULYSASNC YSILELYSGL YGLUALAARG  780
LEUASNTHRA LALEUILEAR GILESERTHR SERSERSERP HEASPASNSE RLEUSERPRO  840
LEUASNASPG LYGLNTHRTH RARGSERPHE LYSILEASNA LALYSLYSTR PTRPTHRILE  900
PHETYRTHRI LEILEASPTY RILEASNTHR ILEVALGLNT HRMETALAPR OARGHISARG  960
ALAILETYRP ROGLUGLYTR PMETLEUARG TYRALALYSG LYGLUASNLE UTYRPHEGLN  1020
GLYHISHISH ISHISHISHI S                                            1041

SEQ ID NO: 9            moltype = DNA  length = 2294
FEATURE                 Location/Qualifiers
source                  1..2294
                        mol_type = other DNA
                        organism = Rotavirus C
SEQUENCE: 9
accgagctcg aattcatggc atcaagcttg taccagcaat tgatttcgca gaattattac  60
tctaccggca acgagatact tctcgataag caaacgacac gcacaactaa ggattttgta  120
gaagcaggaa attatactta cgctcaactg ccacctacgg aatggggcgc aggctcgaca  180
tttgagtcca cgtttaaaag ttctaatata acaggtcctc atagcaatgc cgttattgag  240
tggaataacc tcataaattc ggatatctgg gtattgtacc agaagccact cgacatcacc  300
gttccaatcc gtttgctcaa gcacggcccc gagaattacg gaaatgtagc ggcgtttgag  360
ttgtggtacg gtaaggcggg tcatactgtt actagcattt actactccgc gattagtaac  420
ccaaataaca cggttacgtt gacttctgat agtttggtgc ttttctggaa cgaaggtcaa  480
actacccttg ataaaaagac tgttaacttt aattggaata tgggcggaat tttggtccgt  540
cctagtagag gaacgagagt agatatctgt atgtcgaaca tggataacac agatgatgca  600
tcatttaatt ggattcagtg gaaacacgag ttcccgagat cctcaaattc agctaacgtc  660
aacatgtatg tagaatacta ccttgcatcc agcgatccat atcacgagtt gaaagagctc  720
caacgcccta cagtgacgac catcaatatg caaatgatga aagcagtgaa cggtgacttg  780
atcaatgtag acgaggttat ctccaaagac tccctttggc aagagatgcg ctatgttagg  840
gatataactc tcgagtgtaa gatcgagtct gaagttatta aaggcggtgg ctggggctat  900
gattacacaa gcatcacctt caaaaccgta aatcacacat acagttacaa ccgcgccggc  960
gagaatgtga ccgcccacgt gacagtgtcc ttcaataaca tgaaggaacg ctcctacgga  1020
ggctcacttc ctacggattt caagataaac aggtttgacg tgatggatat cgacacctat  1080
atgtatattg actattggga cgactccgat atgttcaaga acatggttta tgtacgcgat  1140
ctcagggcag atgtgaacgg cttcttttac tataaagaga tgtcctattc gtttagaatc  1200
cccgttggtg tacacccaag gataaatagt agtggtatcg agttcacgta cgaaaagtgc  1260
atgttgagtc aacagttcac cgaccagttg gcactgaaca gcatgaggtt tgtatttcgc  1320
gttacatctg cgaacggctg gtttatgacc tcaggcggac ccaatacgag gcgcatagct  1380
tcaggcactg gcttcgcata tagtgatggc cacacttcga gaacagtcgg tacactcagt  1440
ttcatctcgc tcatcccttc taatcccaac taccagacgc ccatagctag ctcctcgacg  1500
gtcaggatgg accttgaccg caagattaac gatctgagga acgatttcaa ccagctcgcg  1560
agctccgtcg cactcggaga cattatgtct ctggctatgt cacctctcac tttttctaat  1620
cttctggagt cggtaccggc aataactagt agtgtgaaag atgttgccgc caacgtaatg  1680
aaaaaatttc gtaacactaa gatgtttaag aaagccacaa aacctaaata taaggagttc  1740
atcattggtg atttgcttga ggatgtaacg aatgtgacca agaactccaa taccatgaac  1800
tttgacgata tcacgtctgc cgtgatgata agtacgacaa acaagctgca attgactgac  1860
gtagacaccc tgtcagaaat tgtcgttagg tctgcagatg actttatacc gtcccgtagc  1920
taccgcatga tcgagaataa cacggtgtat gaagcgacac catcacgtgt gttttcttac  1980
gatcttgcaa ccatgcagca gagagacttc gacattgata agtttattca gcttgcttca  2040
aagtcacccg taatttcagc gatcgttgat ttcgccacac tgaaggccat gagggagacg  2100
tatggaacat cggtcgaagt gattcataag cttgtggcct cggattctcc aacaatattg  2160
tctttcatca ataataacaa tccacttatc aggaacagga tcgaagaact gctcagacag  2220
tgccgcatta agggcgaaaa cttgtacttt caaggccatc accatcacca tcactaggcg  2280
gccgcttaat taat                                                    2294

SEQ ID NO: 10           moltype = AA  length = 2259
FEATURE                 Location/Qualifiers
source                  1..2259
                        mol_type = protein
                        organism = Rotavirus C
SEQUENCE: 10
METALASERS ERLEUTYRGL NGLNLEUILE SERGLNASNT YRTYRSERTH RGLYASNGLU  60
ILELEULEUA SPLYSGLNTH RTHRARGTHR THRLYSASPP HEVALGLUAL AGLYASNTYR  120
THRTYRALAG LNLEUPROPR OTHRGLUTRP GLYALAGLYS ERTHRPHEGL USERTHRPHE  180
LYSSERSERA SNILETHRGL YPROHISSER ASNALAVALI LEGLUTRPAS NASNLEUILE  240
ASNSERASPI LETRPVALLE UTYRGLNLYS PROLEUASPI LETHRVALPR OILEARGLEU  300
LEULYSHISG LYPROGLUAS NTYRGLYASN VALALAALAP HEGLULEUTR PTYRGLYLYS  360
ALAGLYHIST HRVALTHRSE RILETYRTYR SERALAILES ERASNPROAS NASNTHRVAL  420
THRLEUTHRS ERASPSERLE UVALLEUPHE TRPASNGLUG LYGLNTHRTH RLEUASPLYS  480
LYSTHRVALA SNPHEASNTR PASNMETGLY GLYILELEUV ALARGPROSE RARGGLYTHR  540
ARGVALASPI LECYSMETSE RASNMETASP ASNTHRASPA SPALASERPH EASNTRPILE  600
GLNTRPLYSH ISGLUPHEPR OARGSERSER ASNSERALAA SNVALASNME TTYRVALGLU  660
TYRTYRLEUA LASERSERAS PPROTYRHIS GLULEULYSG LULEUGLNAR GPROTHRVAL  720
THRTHRILEA SNMETGLNME TMETLYSALA VALASNGLYA SPLEUILEAS NVALASPGLU  780
VALILESERL YSASPSERLE UTRPGLNGLU METARGTYRV ALARGASPIL ETHRLEUGLU  840
CYSLYSILEG LUSERGLUVA LILELYSGLY GLYGLYTRPG LYTYRASPTY RTHRSERILE  900
THRPHELYST HRVALASNHI STHRTYRSER TYRASNARGA LAGLYGLUAS NVALTHRALA  960
HISVALTHRV ALSERPHEAS NASNMETLYS GLUARGSERT YRGLYGLYSE RLEUPROTHR  1020
ASPPHELYSI LEASNARGPH EASPVALMET ASPILEASPT HRTYRMETTY RILEASPTYR  1080
TRPASPASPS ERASPMETPH ELYSASNMET VALTYRVALA RGASPLEUAR GALAASPVAL  1140
ASNGLYPHEP HETYRTYRLY SGLUMETSER TYRSERPHEA RGILEPROVA LGLYVALHIS  1200
```

```
PROARGILEA SNSERSERGL YILEGLUPHE THRTYRGLUL YSCYSMETLE USERGLNGLN  1260
PHETHRASPG LNLEUALALE UASNSERMET ARGPHEVALP HEARGVALTH RSERALAASN  1320
GLYTRPPHEM ETTHRSERGL YGLYPROASN THRARGARGI LEALASERGL YTHRGLYPHE  1380
ALATYRSERA SPGLYHISTH RSERARGTHR VALGLYTHRL EUSERPHEIL ESERLEUILE  1440
PROSERASNP ROASNTYRGL NTHRPROILE ALASERSERS ERTHRVALAR GMETASPLEU  1500
ASPARGLYSI LEASNASPLE UARGASNASP PHEASNGLNL EUALASERSE RVALALALEU  1560
GLYASPILEM ETSERLEUAL AMETSERPRO LEUTHRPHES ERASNLEULE UGLUSERVAL  1620
PROALAILET HRSERSERVA LLYSASPVAL ALAALAASNV ALMETLYSLY SPHEARGASN  1680
THRLYSMETP HELYSLYSAL ATHRLYSPRO LYSTYRLYSG LUPHEILEIL EGLYASPLEU  1740
LEUGLUASPV ALTHRASNVA LTHRLYSASN SERASNTHRM ETASNPHEAS PASPILETHR  1800
SERALAVALM ETILESERTH RTHRASNLYS LEUGLNLEUT HRASPVALAS PTHRLEUSER  1860
GLUILEVALV ALARGSERAL AASPASPPHE ILEPROSERA RGSERTYRAR GMETILEGLU  1920
ASNASNTHRV ALTYRGLUAL ATHRPROSER ARGVALPHES ERTYRASPLE UALATHRMET  1980
GLNGLNARGA SPPHEASPIL EASPLYSPHE ILEGLNLEUA LASERLYSSE RPROVALILE  2040
SERALAILEV ALASPPHEAL ATHRLEULYS ALAMETARGG LUTHRTYRGL YTHRSERVAL  2100
GLUVALILEH ISLYSLEUVA LALASERASP SERPROTHRI LELEUSERPH EILEASNASN  2160
ASNASNPROL EUILEARGAS NARGILEGLU GLULEULEUA RGGLNCYSAR GILELYSGLY  2220
GLUASNLEUT YRPHEGLNGL YHISHISHIS HISHISHIS                         2259

SEQ ID NO: 11          moltype = DNA  length = 2414
FEATURE                Location/Qualifiers
source                 1..2414
                       mol_type = other DNA
                       organism = Rotavirus A
SEQUENCE: 11
accgagctcg aattcatggc aagccttatc tacagacagc tgctgacgaa cagctacaca  60
atcgatctta gtgacgaaat tgaagaaatc ggatcgctca aatcacagga cgtcacaata  120
aaccctggcc catttgctca gacaggttat gcgcctgtga gctggggccc tggcgagacg  180
aacgattcaa cgaccatcga gccggttctg gatggcccat atcgcccgac cacctttaac  240
cccccgatag aatactggac gctgtttgcg cctaataaca aaggagtcgt tgccgaactt  300
acgaacaacg cggatatctg gttggcgatc atccttatag agccaaacgc ttcaagggag  360
attcgcactt ataccatctt cggtcaacag gtcaatttga cggtcgagaa tgtatcccaa  420
actaagtgga aatttgtgga tttccgtcgc cgctcgcaac acgacactta tgtccttgaa  480
ggaactcttc ttagtgatac taaattgcag gccgccatga aatatggtgc taggctgttt  540
actttcatag gtgatactcc ttccgcagcg cctcaggaat acggttacga gactaataac  600
tattcggccg ttgaggtaaa gtcattttgc gacttctaca tgattccccg cttgcctaga  660
gaggtgtgca gaaactatat caaccaagga cttccgccta tacagaatac ccgcaacgtt  720
gtacccgttg cattgtcggc tcgttcggtt atagcgcagc gtgtttcagt taatgaggac  780
atagtgatat cgaagacatc cctctggaaa gagatgcagt acaataggga tataaccatc  840
aggttcaagt tcgctaacca aataatcaaa tcgggcggac tgggttataa atgggccgag  900
atatcatttc gtcctgcaaa ctatcaatat acctatattc gtgacggcga ggaggtaacc  960
gcgcacacta cctgttcggt gaacggcgta aacaatttct cctacaacgg cggttccctc  1020
ccaacggact tcgtcatatc gaggtatgag gttctcaaag agaactcgtt cgtttacatc  1080
gattactggg atgatagcca agcctttcgt aacatggtgt acgtcaggtc actggcaacg  1140
gacctcaact cgatcacatg ctcgggaggc agttataatt ttgcgctccc acttggcaac  1200
ttcccagtga tgtctggcgg tgccgtgtct ctccacccga gcggtgtgac gctcagcacg  1260
cagtttacag actacgtgag cctcaatagt ctgaggttcc gctttagact ggcggttgaa  1320
gagccaccgt tctccattac cagaacaaga gtttctcgct tgtacggact tccagctgtc  1380
aacccgaata acaacaagga tttttatgaa atggcgggaa gattctcatt gatctctctt  1440
gtaccatcaa atgacgatta ccaaactccg ataatgaata gcgtcacagt tagacaagat  1500
ttggaaaggc agttgggaga acttcgtgat gaatttaacg ccctctcaca gcaaatcgca  1560
atgagccagt tgatagatct tgcactgctt ccgctggaca tgttctctat gtttagcggt  1620
atcaagggca cgatagacat cgcaaaaagt atggcgacaa aggtcatgaa gaagttccgt  1680
aagtccaatc tcgcaaatag catttccacg cttacggaat cgttgtcaga tgccgcgtcg  1740
agcatcagta gaggctccac aatccgcagt atcggctcta gcgcttcggc gtggaccgag  1800
gtaagtacaa cgatagcaga cacaacaaat gcaacgaaca gcatagcaac tcagacagca  1860
actatctcca agaggctccg cttgaaagaa atatcaactc aaaccgacgg aatgaatttc  1920
gatgatatct ctgctgctgt gctgaagact aaaatagaca agtcaactca aatcgcgccc  1980
aacacactgc ctgacatcgt tacagaggcc tccgaaaagt ttataccaaa tagggcttat  2040
cgcgtcatcg acaatgacga ggtattcgaa gcgggcacgg acggacgctt tttcgcctac  2100
agagtcgaaa cgttcgagga gataccgttc gatgtacaga agttcgcgga ccttgtgacc  2160
gattcaccag ttatttcagc aataatagac tttaaaactc tgaagaacct caacgataat  2220
tatggcatca ccaagcaaca ggcgtacaac cttcttcgta gcgacccgag ggtcctcagg  2280
gagttcataa accaggaaaa cccgataatc cgcaaccgta tcgaatcttt gattatgcaa  2340
tgcaggttga agggcgaaaa cttgtacttt caaggccatc accatcacca tcactaggcg  2400
gccgcttaat taat                                                    2414

SEQ ID NO: 12          moltype = AA  length = 2379
FEATURE                Location/Qualifiers
source                 1..2379
                       mol_type = protein
                       organism = Rotavirus A
SEQUENCE: 12
METALASERL EUILETYRAR GGLNLEULEU THRASNSERT YRTHRILEAS PLEUSERASP  60
GLUILEGLUG LUILEGLYSE RLEULYSSER GLNASPVALT HRILEASNPR OGLYPROPHE  120
ALAGLNTHRG LYTYRALAPR OVALSERTRP GLYPROGLYG LUTHRASNAS PSERTHRTHR  180
ILEGLUPROV ALLEUASPGL YPROTYRARG PROTHRTHRP HEASNPROPR OILEGLUTYR  240
TRPTHRLEUP HEALAPROAS NASNLYSGLY VALVALALAG LULEUTHRAS NASNALAASP  300
ILETRPLEUA LAILEILELE UILEGLUPRO ASNALASERA RGGLUILEAR GTHRTYRTHR  360
```

```
ILEPHEGLYG LNGLNVALAS NLEUTHRVAL GLUASNVALS ERGLNTHRLY STRPLYSPHE  420
VALASPPHEA RGARGARGSE RGLNHISASP THRTYRVALL EUGLUGLYTH RLEULEUSER  480
ASPTHRLYSL EUGLNALAAL AMETLYSTYR GLYALAARGL EUPHETHRPH EILEGLYASP  540
THRPROSERA LAALAPROGL NGLUTYRGLY TYRGLUTHRA SNASNTYRSE RALAVALGLU  600
VALLYSSERP HECYSASPPH ETYRMETILE PROARGLEUP ROARGGLUVA LCYSARGASN  660
TYRILEASNG LNGLYLEUPR OPROILEGLN ASNTHRARGA SNVALVALPR OVALALALEU  720
SERALAARGS ERVALILEAL AGLNARGVAL SERVALASNG LUASPILEVA LILESERLYS  780
THRSERLEUT RPLYSGLUME TGLNTYRASN ARGASPILET HRILEARGPH ELYSPHEALA  840
ASNGLNILEI LELYSSERGL YGLYLEUGLY TYRLYSTRPA LAGLUILESE RPHEARGPRO  900
ALAASNTYRG LNTYRTHRTY RILEARGASP GLYGLUGLUV ALTHRALAHI STHRTHRCYS  960
SERVALASNG LYVALASNAS NPHESERTYR ASNGLYGLYS ERLEUPROTH RASPPHEVAL  1020
ILESERARGT YRGLUVALLE ULYSGLUASN SERPHEVALT YRILEASPTY RTRPASPASP  1080
SERGLNALAP HEARGASNME TVALTYRVAL ARGSERLEUA LATHRASPLE UASNSERILE  1140
THRCYSSERG LYGLYSERTY RASNPHEALA LEUPROLEUG LYASNPHEPR OVALMETSER  1200
GLYGLYALAV ALSERLEUHI SPROSERGLY VALTHRLEUS ERTHRGLNPH ETHRASPTYR  1260
VALSERLEUA SNSERLEUAR GPHEARGPHE ARGLEUALAV ALGLUGLUPR OPROPHESER  1320
ILETHRARGT HRARGVALSE RARGLEUTYR GLYLEUPROA LAVALASNPR OASNASNASN  1380
LYSASPPHET YRGLUMETAL AGLYARGPHE SERLEUILES ERLEUVALPR OSERASNASP  1440
ASPTYRGLNT HRPROILEME TASNSERVAL THRVALARGG LNASPLEUGL UARGGLNLEU  1500
GLYGLULEUA RGASPGLUPH EASNALALEU SERGLNGLNI LEALAMETSE RGLNLEUILE  1560
ASPLEUALAL EULEUPROLE UASPMETPHE SERMETPHES ERGLYILELY SGLYTHRILE  1620
ASPILEALAL YSSERMETAL ATHRLYSVAL METLYSLYSP HEARGLYSSE RASNLEUALA  1680
ASNSERILES ERTHRLEUTH RGLUSERLEU SERASPALAA LASERSERIL ESERARGGLY  1740
SERTHRILEA RGSERILEGL YSERSERALA SERALATRPT HRGLUVALSE RTHRTHRILE  1800
ALAASPTHRT HRASNALATH RASNSERILE ALATHRGLNT HRALATHRIL ESERLYSARG  1860
LEUARGLEUL YSGLUILESE RTHRGLNTHR ASPGLYMETA SNPHEASPAS PILESERALA  1920
ALAVALLEUL YSTHRLYSIL EASPLYSSER THRGLNILEA LAPROASNTH RLEUPROASP  1980
ILEVALTHRG LUALASERGL ULYSPHEILE PROASNARGA LATYRARGVA LILEASPASN  2040
ASPGLUVALP HEGLUALAGL YTHRASPGLY ARGPHEPHEA LATYRARGVA LGLUTHRPHE  2100
GLUGLUILEP ROPHEASPVA LGLNLYSPHE ALAASPLEUV ALTHRASPSE RPROVALILE  2160
SERALAILEI LEASPPHELY STHRLEULYS ASNLEUASNA SPASNTYRGL YILETHRLYS  2220
GLNGLNALAT YRASNLEULE UARGSERASP PROARGVALL EUARGGLUPH EILEASNGLN  2280
GLUASNPROI LEILEARGAS NARGILEGLU SERLEUILEM ETGLNCYSAR GLEULYSGLY  2340
GLUASNLEUT YRPHEGLNGL YHISHISHIS HISHISHIS                         2379

SEQ ID NO: 13          moltype = DNA  length = 2279
FEATURE                Location/Qualifiers
source                 1..2279
                       mol_type = other DNA
                       organism = Rotavirus C
SEQUENCE: 13
accgagctcg aattcatggc tagcagcctt taccatcagc tcatttctca gaattattac  60
agtacaggaa acgagatcct taaagatttg caaactacta aaacaacagt cgactacgta  120
gacgctggca actacacata ttctcagctt ccgcccacca aatggggtgc tggcgccact  180
tttgaatctt ttttttcggc cgccgaaatc accggccctc ataccaatag ggttatcgaa  240
tggaagaacc ttcttaatag caatcagtgg ctccttttcc ctaaaccaac agacactgtc  300
aagctcttga agcatggtcc tcagacgtat gacaatactt tggctgcatg cgagctttgg  360
tatggaaagg ctaatactac agtgacgtct gaacattact cgtctctgtc agactcttgg  420
gtcaacgtta acagcgattc actcgtactc ttctggaacg ctggcggcac cacattcaac  480
aaaaaggtcg tcaatttcgc ctggaacatg ggaggtatca tgataaaacc ttcatcgcaa  540
cttcctcgtc tcgaaattta tatggccaac atgaacaatt tcaatggcga taacttcaat  600
tgggaggagt ggcatttcac ccttcctagg tctaatgcaa ctatcaatat atatattgac  660
tattacctgg cttccagtga cccgtataat cagcttaagg agctccaaca gcccacgatt  720
actacgttcg agatgcgcat gatgcttctg aatagagatg gtcaaatcaa cgtaaatgaa  780
gtagtcagca aagattcact ctggcaggaa atgcgctacg cgcgtgacat cacactccaa  840
tgcaagatcg agtccgaggt ggtgaaaggt ggcggttggg gttatgacta tacatctatc  900
aggttcaaga ctgttaacca tacgtacagt tacactagag cgggcgaaaa cgttaatgca  960
catgtcacga tatcgttcaa taatctgaaa gagagaagct acggaggttc gcttccgacg  1020
gatttcaaga taggtaagtt cgatataata gatgtagata cgtatatgta cattgactac  1080
tgggatgatt ccgagatttt caagaacatg gtatacgtaa gagatctcac cgcgaatatt  1140
ggtgacttct tccattatag agagatgagc tattatttcc aaataccggt cggagttcat  1200
cctggtattc acagcagtgg tgtcaggttc atgtacgaaa ggtgcctttt gtctcagcaa  1260
tttacggatc aagttgcttt gaactcgatg aggttcattt tcaaagtaac ggcggctaac  1320
ggctggttca tgacgagcgg aaatattaat actcgtagga tagcgagcgg cacaggcttt  1380
gcttacgcca atggttacgt gtcacagacc gtgggcaaca tcagcttcat tagccttatt  1440
ccctcgaacc ctaattatca gacacccatc gcctccagct ccaccgtccg tatggacttg  1500
gagcgtaaga ttaatgatct taggaatgac tttaaccaac tggcatcctc agtggctctc  1560
ggagatatcc tgtcgcttgc cacctcgccg ctcacattgg ctaacctgtt ggagtcagtg  1620
cctgcagtag ctagctccgt gaaggatgtg gcggcgaatg taatgaaaag gttcagaaat  1680
actaaaatgt ttaaacgtgc cgcgaaaccc aaatataaag agttcatcat aggtgatctt  1740
cttgaggatg taaccaatgt gacccgtaat cccaactcta tgaatttcga tgatatcacg  1800
agtgccatga tgatttccac tacaaacaaa cttcaattga cggatgtgga cacccttttct  1860
gagatcgttg ccaggtctgc tgatgacttc attccgaata ggtcctaccg tatgatcgaa  1920
aacggagttg tccatgaagc aacacaaaat ggtgtttttt cgtatgatct tgtaactctg  1980
cagcaacgtt ctttcgacat ggataaattt cttcaacttg ctagcaagtc acctgttatt  2040
tcggccatag ttgatttcgc gacccttaag gcaatgaggg acacgtatgg catcggtaca  2100
gatgtacttt acaaattggt tgtaagtgat acgccaaccc ttctgtcatt tattaataac  2160
aacaatccac tcatccgcaa taggatcgaa ggactgctga ggcaatgtag aattaagggc  2220
gaaaacttgt actttcaagg ccatcaccat caccatcact aggcggccgc ttaattaat   2279
```

```
SEQ ID NO: 14          moltype = AA  length = 2244
FEATURE                Location/Qualifiers
source                 1..2244
                       mol_type = protein
                       organism = Rotavirus C
SEQUENCE: 14
METALASERS ERLEUTYRHI SGLNLEUILE SERGLNASNT YRTYRSERTH RGLYASNGLU  60
ILELEULYSA SPLEUGLNTH RTHRLYSTHR THRVALASPT YRVALASPAL AGLYASNTYR  120
THRTYRSERG LNLEUPROPR OTHRLYSTRP GLYALAGLYA LATHRPHEGL USERPHEPHE  180
SERALAALAG LUILETHRGL YPROHISTHR ASNARGVALI LEGLUTRPLY SASNLEULEU  240
ASNSERASNG LNTRPLEULE UPHEPROLYS PROTHRASPT HRVALLYSLE ULEULYSHIS  300
GLYPROGLNT HRTYRASPAS NTHRLEUALA ALACYSGLUL EUTRPTYRGL YLYSALAASN  360
THRTHRVALT HRSERGLUHI STYRSERSER LEUSERASPS ERTRPVALAS NVALASNSER  420
ASPSERLEUV ALLEUPHETR PASNALAGLY GLYTHRTHRP HEASNLYSLY SVALVALASN  480
PHEALATRPA SNMETGLYGL YILEMETILE LYSPROSERS ERGLNLEUPR OARGLEUGLU  540
ILETYRMETA LAASNMETAS NASNPHEASN GLYASPASNP HEASNTRPGL UGLUTRPHIS  600
PHETHRLEUP ROARGSERAS NALATHRILE ASNILETYRI LEASPTYRTY RLEUALASER  660
SERASPPROT YRASNGLNLE ULYSGLULEU GLNGLNPROT HRILETHRTH RPHEGLUMET  720
ARGMETMETL EULEUASNAR GASPGLYGLN ILEASNVALA SNGLUVALVA LSERLYSASP  780
SERLEUTRPG LNGLUMETAR GTYRALAARG ASPILETHRL EUGLNCYSLY SILEGLUSER  840
GLUVALVALL YSGLYGLYGL YTRPGLYTYR ASPTYRTHRS ERILEARGPH ELYSTHRVAL  900
ASNHISTHRT YRSERTYRTH RARGALAGLY GLUASNVALA SNALAHISVA LTHRILESER  960
PHEASNASNL EULYSGLUAR GSERTYRGLY GLYSERLEUP ROTHRASPPH ELYSILEGLY  1020
LYSPHEASPI LEILEASPVA LASPTHRTYR METTYRILEA SPTYRTRPAS PASPSERGLU  1080
ILEPHELYSA SNMETVALTY RVALARGASP LEUTHRALAA SNILEGLYAS PPHEPHEHIS  1140
TYRARGGLUM ETSERTYRTY RPHEGLNILE PROVALGLYV ALHISPROGL YILEHISSER  1200
SERGLYVALA RGPHEMETTY RGLUARGCYS LEULEUSERG LNGLNPHETH RASPGLNVAL  1260
ALALEUASNS ERMETARGPH EILEPHELYS VALTHRALAA LAASNGLYTR PPHEMETTHR  1320
SERGLYASNI LEASNTHRAR GARGILEALA SERGLYTHRG LYPHEALATY RALAASNGLY  1380
TYRVALSERG LNTHRVALGL YASNILESER PHEILESERL EUILEPROSE RASNPROASN  1440
TYRGLNTHRP ROILEALASE RSERSERTHR VALARGMETA SPLEUGLUAR GLYSILEASN  1500
ASPLEUARGA SNASPPHEAS NGLNLEUALA SERSERVALA LALEUGLYAS PILELEUSER  1560
LEUALATHRS ERPROLEUTH RPHEALAASN LEULEUGLUS ERVALPROAL AVALALASER  1620
SERVALLYSA SPVALALAAL AASNVALMET LYSARGPHEA RGASNTHRLY SMETPHELYS  1680
ARGALAALAL YSPROLYSTY RLYSGLUPHE ILEILEGLYA SPLEULEUGL UASPVALTHR  1740
ASNVALTHRA RGASNPROAS NSERMETASN PHEASPASPI LETHRSERAL AMETMETILE  1800
SERTHRTHRA SNLYSLEUGL NLEUTHRASP VALASPTHRL EUSERGLUIL EVALALAARG  1860
SERALAASPA SPPHEILEPR OASNARGSER TYRARGMETI LEGLUASNGL YVALVALHIS  1920
GLUALATHRG LNASNGLYVA LPHESERTYR ASPLEUVALT HRLEUGLNGL NARGSERPHE  1980
ASPMETASPL YSPHELEUGL NLEUALASER LYSSERPROV ALILESERAL AILEVALASP  2040
PHEALATHRL EULYSALAME TARGASPTHR TYRGLYILEG LYTHRASPVA LLEUTYRLYS  2100
LEUVALVALS ERASPTHRPR OTHRLEULEU SERPHEILEA SNASNASNAS NPROLEUILE  2160
ARGASNARGI LEGLUGLYLE ULEUARGGLN CYSARGILEL YSGLYGLUAS NLEUTYRPHE  2220
GLNGLYHISH ISHISHISHI SHIS                                         2244

SEQ ID NO: 15          moltype = DNA  length = 2276
FEATURE                Location/Qualifiers
source                 1..2276
                       mol_type = other DNA
                       organism = Rotavirus C
SEQUENCE: 15
accgagctcg aattcatggc aagttcattg tataagcaac tgataagcca aaactattat  60
agtacgggca acgacatcct gctcgatcgc cagacgaacg agacaactgt cgattacgtt  120
gatattggta attactcgta cacccaactg ccccctacta gttggggtgc gggcatgacg  180
ttcaagtcgg ccttcaacgc cgaagagatt accggtccta acactggtga tatagatttg  240
aataacctca caaacgccaa cggttggatt ctctatgaca aacctacctc aacgaagcgc  300
ttgcttaaac tgggtcccga ccgttacgat aacgtatatg cggctttcga gctctggtat  360
ggaaaagcta ataccatcgt agagtccatc tattatgcct ctgcgcaaaa ctccgagaaa  420
accgctacgg tccagtatga ctctctcgta ctgttcttta atgttggata tacaggtctt  480
actaaacaga tcgtgaaatt caactggaac atgggaggaa ttttggttag gccgacagca  540
gacggccgtg tggatgtctg catggcggac atgaatgact ttaactcaga caatttcaat  600
tgggaagcct ggaagcgctc tttcccgcgt agtaatatca atatgtatac agaatactat  660
ctcgcaaatg ttgatccgta taaccagctg aaggctctca atcagctcac cgctaaaaat  720
atagagctta gaatgatgaa agcaacaaag caacagggac caattaatgt ggatgaggtc  780
gtttccaaag attcattgtg gcaggagatg aggtatgcta gagatatcac acttaagtgt  840
aagatcgaat cggacatcat taaaggcggc ggttggggct atgactatac aagcatcacg  900
ttcaaaactg tgaactacgt gtacaaatac acccgttctg gagaggaggt caatgcccac  960
gtgacaattt cattcaacaa catgaaagaa cgcagctatg gcggttcact tcccactgac  1020
ttcaagatca agagattcga cgttattgat aacgatacgt atatgtatat cgattattgg  1080
gacgactcag atatatttaa gaatatggtc tacgtacgcg acctgagggc aaacatgggt  1140
gactttttct attatagtga gatgtggcac agatttccaa ttccagtagg aacccaccca  1200
ggcctgcatt ccagcggcgt ccaatttaca tacgaaaaat gtttgttgag ccaacagttc  1260
acagatatgg ttgcgttgaa ctcgatgcgc ttcattttcc gcgttacctc gtccaacggt  1320
tggtatatca cttccggagg tccaaatacg cgcaaagtag cttcgggaac cggattcgcg  1380
tactcaaacg gctacataag tgagactgtc ggaaacatta gctttatctc attgattcct  1440
tctaatccta attatcagac accgattgca tcgtcctcga cagtaaggat ggatcttgac  1500
cgtaaaatta acgacctccg caatgacttt aacaatctgg ctagctctgt cgccttggga  1560
gacataatgt cattggcaat gtcacccctg acatttgcga acctgcttga gtcggtccca  1620
```

-continued

```
gcgataacta gtagcgtcaa agatgtcgca gccaacgtaa tgaagaagtt taggaatact  1680
aagatgttca agcgtgccac aaagacgaag tacaaggaat acatcatcgg cgacctcctg  1740
gaagacgtga caaatgtcac gagggatgta aacaagatga atttcgacga tatcacttcg  1800
gcgatgatgg tgtcagcgac caataaactg caactgactg atattgatac atttagtgaa  1860
attgtagtga ggtccgcaga cgactttata ccaaacaggt cttacaggat gatcgagaat  1920
ggtatcgtac atgaggctac cccaactaga gtcttctctt atgaccttaa aaccctgcaa  1980
caaaccgact tcgatatgga caaattcatg caattggcct ccgagtctcc ggtcatatcg  2040
gcaataatag actttgcaac gctgaaggcc atgcgtgaca cttatggtat atcgactgat  2100
ataatgtaca aacttatagc aagcgactcg cctactattc tgtcttttat caacaacaat  2160
aaccctctta taagaaatag aatcgagggt ttgcttcgtc aatgcagaat taagggcgaa  2220
aacttgtact ttcaaggcca tcaccatcac catcactagg cggccgctta attaat      2276

SEQ ID NO: 16          moltype = AA  length = 2241
FEATURE                Location/Qualifiers
source                 1..2241
                       mol_type = protein
                       organism = Rotavirus C
SEQUENCE: 16
METALASERS ERLEUTYRLY SGLNLEUILE SERGLNASNT YRTYRSERTH RGLYASNASP  60
ILELEULEUA SPARGGLNTH RASNGLUTHR THRVALASPT YRVALASPIL EGLYASNTYR  120
SERTYRTHRG LNLEUPROPR OTHRSERTRP GLYALAGLYM ETTHRPHELY SSERALAPHE  180
ASNALAGLUG LUILETHRGL YPROASNTHR GLYASPILEA SPLEUASNAS NLEUTHRASN  240
ALAASNGLYT RPILELEUTY RASPLYSPRO THRSERTHRL YSARGLEULE ULYSLEUGLY  300
PROASPARGT YRASPASNVA LTYRALAALA PHEGLULEUT RPTYRGLYLY SALAASNTHR  360
ILEVALGLUS ERILETYRTY RALASERALA GLNASNSERG LULYSTHRAL ATHRVALGLN  420
TYRASPSERL EUVALLEUPH EPHEASNVAL GLYTYRTHRG LYLEUTHRLY SGLNILEVAL  480
LYSPHEASNT RPASNMETGL YGLYILELEU VALARGPROT HRALAASPGL YARGVALASP  540
VALCYSMETA LAASPMETAS NASPPHEASN SERASPASNP HEASNTRPGL UALATRPLYS  600
ARGSERPHEP ROARGSERAS NILEASNMET TYRTHRGLUT YRTYRLEUAL AASNVALASP  660
PROTYRASNG LNLEULYSAL ALEUASNGLN LEUTHRALAL YSASNILEGL ULEUARGMET  720
METLYSALAT HRLYSGLNGL NGLYPROILE ASNVALASPG LUVALVALSE RLYSASPSER  780
LEUTRPGLNG LUMETARGTY RALAARGASP ILETHRLEUL YSCYSLYSIL EGLUSERASP  840
ILEILELYSG LYGLYGLYTR PGLYTYRASP TYRTHRSERI LETHRPHELY STHRVALASN  900
TYRVALTYRL YSTYRTHRAR GSERGLYGLU GLUVALASNA LAHISVALTH RILESERPHE  960
ASNASNMETL YSGLUARGSE RTYRGLYGLY SERLEUPROT HRASPPHELY SILELYSARG  1020
PHEASPVALI LEASPASNAS PTHRTYRMET TYRILEASPT YRTRPASPAS PSERASPILE  1080
PHELYSASNM ETVALTYRVA LARGASPLEU ARGALAASNM ETGLYASPPH EPHETYRTYR  1140
SERGLUMETT RPHISARGPH EPROILEPRO VALGLYTHRH ISPROGLYLE UHISSERSER  1200
GLYVALGLNP HETHRTYRGL ULYSCYSLEU LEUSERGLNG LNPHETHRAS PMETVALALA  1260
LEUASNSERM ETARGPHEIL EPHEARGVAL THRSERSERA SNGLYTRPTY RILETHRSER  1320
GLYGLYPROA SNTHRARGLY SVALALASER GLYTHRGLYP HEALATYRSE RASNGLYTYR  1380
ILESERGLUT HRVALGLYAS NILESERPHE ILESERLEUI LEPROSERAS NPROASNTYR  1440
GLNTHRPROI LEALASERSE RSERTHRVAL ARGMETASPL EUASPARGLY SILEASNASP  1500
LEUARGASNA SPPHEASNAS NLEUALASER SERVALALAL EUGLYASPIL EMETSERLEU  1560
ALAMETSERP ROLEUTHRPH EALAASNLEU LEUGLUSERV ALPROALAIL ETHRSERSER  1620
VALLYSASPV ALALAALAAS NVALMETLYS LYSPHEARGA SNTHRLYSME TPHELYSARG  1680
ALATHRLYST HRLYSTYRLY SGLUTYRILE ILEGLYASPL EULEUGLUAS PVALTHRASN  1740
VALTHRARGA SPVALASNLY SMETASNPHE ASPASPILET HRSERALAME TMETVALSER  1800
ALATHRASNL YSLEUGLNLE UTHRASPILE ASPTHRPHES ERGLUILEVA LVALARGSER  1860
ALAASPASPP HEILEPROAS NARGSERTYR ARGMETILEG LUASNGLYIL EVALHISGLU  1920
ALATHRPROT HRARGVALPH ESERTYRASP LEULYSTHRL EUGLNGLNTH RASPPHEASP  1980
METASPLYSP HEMETGLNLE UALASERGLU SERPROVALI LESERALAIL EILEASPPHE  2040
ALATHRLEUL YSALAMETAR GASPTHRTYR GLYILESERT HRASPILEME TTYRLYSLEU  2100
ILEALASERA SPSERPROTH RILELEUSER PHEILEASNA SNASNASNPR OLEUILEARG  2160
ASNARGILEG LUGLYLEULE UARGGLNCYS ARGILELYSG LYGLUASNLE UTYRPHEGLN  2220
GLYHISHISH ISHISHISHI S                                            2241

SEQ ID NO: 17          moltype = DNA  length = 1088
FEATURE                Location/Qualifiers
source                 1..1088
                       mol_type = other DNA
                       organism = Rotavirus C
SEQUENCE: 17
accgagctcg aattcatggt atgtacaacc ctctacacaa tttgtgcaat attgtgcatt  60
ctccttatct atacactgtt tctcagaaag atgttccatt tgcttactga cgcccttgta  120
gttattctta tcatatctgc gtgtgccgga agcagtaatg gccagctctt taccaatgac  180
atcagttacg acggcaacat tgaatctgtg atcaatacaa ctaacccgtt taatgttgag  240
agcctttgta tatactttcc aaacgccgca ataggttcac caggaccggg taaagcagat  300
ggacttctca acgataataa ctacgcccag acacttgcaa cacttttcga aacaaaggga  360
tttcctaagg gatcagtgat attcaagacc tataccaaaa cgagcgactt cattaactct  420
gttgagatga cgtgcagtta taatttggtt ataattccag atgagccaaa aaacagtgaa  480
gcaatagagc agatagccga atggattttg aatgtctggc aatgcgatga catgaatctt  540
gacatctata catacgaaca aatcaataaa gataaccttt gggcagcgtt tggtgaagat  600
tgtgatattt cggtatgtcc gcttgatact acaatgaatg gaatcggctg ctctccggct  660
agtacggaaa cgtatgaagt cgtgtcgaac gatacccagc ttgctttgat agatgtagtt  720
gataatgtca agtatagaat acaaatgtcc agtacactga atcagcttca atgtaagctg  780
aagaattgcg ttaaaggcga accaaggttg aatactgcaa ttatccgtat tagtacgtcc  840
tcttcttttg ataattccct ttctccgctg tcaaacggcc aaaccacgag agcgttcaag  900
atcaatgcta aaaagtggtg gaaaatattc tacactataa tcgattacat caacaccttg  960
```

```
gttcagacga tgaccccaag gcatcgtgct gtctatcctg agggttggat gcttcgctac  1020
gctaagggcg aaaacttgta ctttcaaggc catcaccatc accatcacta ggcggccgct  1080
taattaat                                                           1088

SEQ ID NO: 18          moltype = AA  length = 1053
FEATURE                Location/Qualifiers
source                 1..1053
                       mol_type = protein
                       organism = Rotavirus C
SEQUENCE: 18
METVALCYST HRTHRLEUTY RTHRILECYS ALAILELEUC YSILELEULE UILETYRTHR  60
LEUPHELEUA RGLYSMETPH EHISLEULEU THRASPALAL EUVALVALIL ELEUILEILE  120
SERALACYSA LAGLYSERSE RASNGLYGLN LEUPHETHRA SNASPILESE RTYRASPGLY  180
ASNILEGLUS ERVALILEAS NTHRTHRASN PROPHEASNV ALGLUSERLE UCYSILETYR  240
PHEPROASNA LAALAILEGL YSERPROGLY PROGLYLYSA LAASPGLYLE ULEUASNASP  300
ASNASNTYRA LAGLNTHRLE UALATHRLEU PHEGLUTHRL YSGLYPHEPR OLYSGLYSER  360
VALILEPHEL YSTHRTYRTH RLYSTHRSER ASPPHEILEA SNSERVALGL UMETTHRCYS  420
SERTYRASNL EUVALILEIL EPROASPGLU PROLYSASNS ERGLUALAIL EGLUGLNILE  480
ALAGLUTRPI LELEUASNVA LTRPGLNCYS ASPASPMETA SNLEUASPIL ETYRTHRTYR  540
GLUGLNILEA SNLYSASPAS NLEUTRPALA ALAPHEGLYG LUASPCYSAS PILESERVAL  600
CYSPROLEUA SPTHRTHRME TASNGLYILE GLYCYSSERP ROALASERTH RGLUTHRTYR  660
GLUVALVALS ERASNASPTH RGLNLEUALA LEUILEASPV ALVALASPAS NVALLYSTYR  720
ARGILEGLNM ETSERSERTH RLEUASNGLN LEUGLNCYSL YSLEULYSAS NCYSVALLYS  780
GLYGLUPROA RGLEUASNTH RALAILEILE ARGILESERT HRSERSERSE RPHEASPASN  840
SERLEUSERP ROLEUSERAS NGLYGLNTHR THRARGALAP HELYSILEAS NALALYSLYS  900
TRPTRPLYSI LEPHETYRTH RILEILEASP TYRILEASNT HRLEUVALGL NTHRMETTHR  960
PROARGHISA RGALAVALTY RPROGLUGLY TRPMETLEUA RGTYRALALY SGLYGLUASN  1020
LEUTYRPHEG LNGLYHISHI SHISHISHIS HIS                               1053

SEQ ID NO: 19          moltype = DNA  length = 18
FEATURE                Location/Qualifiers
source                 1..18
                       mol_type = other DNA
                       organism = synthetic construct
SEQUENCE: 19
gtctgcgagc agttgttt                                                18

SEQ ID NO: 20          moltype = DNA  length = 22
FEATURE                Location/Qualifiers
source                 1..22
                       mol_type = other DNA
                       organism = synthetic construct
SEQUENCE: 20
cgctctaaca taccacccta aa                                           22

SEQ ID NO: 21          moltype = DNA  length = 23
FEATURE                Location/Qualifiers
source                 1..23
                       mol_type = other DNA
                       organism = synthetic construct
SEQUENCE: 21
ggatcggtgg tagaccatta ttt                                          23

SEQ ID NO: 22          moltype = DNA  length = 21
FEATURE                Location/Qualifiers
source                 1..21
                       mol_type = other DNA
                       organism = synthetic construct
SEQUENCE: 22
caacgccact accggttatt a                                            21

SEQ ID NO: 23          moltype = DNA  length = 23
FEATURE                Location/Qualifiers
source                 1..23
                       mol_type = other DNA
                       organism = synthetic construct
SEQUENCE: 23
cgaagttcgt tgagttgtct ttc                                          23

SEQ ID NO: 24          moltype = DNA  length = 20
FEATURE                Location/Qualifiers
source                 1..20
                       mol_type = other DNA
                       organism = synthetic construct
SEQUENCE: 24
cctgctgcca accctaataa                                              20

SEQ ID NO: 25          moltype = DNA  length = 21
FEATURE                Location/Qualifiers
```

```
source                  1..21
                        mol_type = other DNA
                        organism = Synthetic construct
SEQUENCE: 25
cgctggatgc aaggtagtat t                                      21

SEQ ID NO: 26           moltype = DNA  length = 22
FEATURE                 Location/Qualifiers
source                  1..22
                        mol_type = other DNA
                        organism = Synthetic construct
SEQUENCE: 26
gtaaggcggg tcatactgtt ac                                     22

SEQ ID NO: 27           moltype = DNA  length = 22
FEATURE                 Location/Qualifiers
source                  1..22
                        mol_type = other DNA
                        organism = Synthetic construct
SEQUENCE: 27
aggagcgttc cttcatgtta tt                                     22

SEQ ID NO: 28           moltype = DNA  length = 19
FEATURE                 Location/Qualifiers
source                  1..19
                        mol_type = other DNA
                        organism = Synthetic construct
SEQUENCE: 28
tggcaagaga tgcgctatg                                         19

SEQ ID NO: 29           moltype = DNA  length = 22
FEATURE                 Location/Qualifiers
source                  1..22
                        mol_type = other DNA
                        organism = Synthetic construct
SEQUENCE: 29
tggtcacatt cgttacatcc tc                                     22

SEQ ID NO: 30           moltype = DNA  length = 23
FEATURE                 Location/Qualifiers
source                  1..23
                        mol_type = other DNA
                        organism = Synthetic construct
SEQUENCE: 30
catctcgctc atcccttcta atc                                    23

SEQ ID NO: 31           moltype = DNA  length = 22
FEATURE                 Location/Qualifiers
source                  1..22
                        mol_type = other DNA
                        organism = Synthetic construct
SEQUENCE: 31
cgttgcgggt attctgtata gg                                     22

SEQ ID NO: 32           moltype = DNA  length = 21
FEATURE                 Location/Qualifiers
source                  1..21
                        mol_type = other DNA
                        organism = Synthetic construct
SEQUENCE: 32
atggtgctag gctgtttact t                                      21

SEQ ID NO: 33           moltype = DNA  length = 22
FEATURE                 Location/Qualifiers
source                  1..22
                        mol_type = other DNA
                        organism = Synthetic construct
SEQUENCE: 33
atgtctatcg tgcccttgat ac                                     22

SEQ ID NO: 34           moltype = DNA  length = 20
FEATURE                 Location/Qualifiers
source                  1..20
                        mol_type = other DNA
                        organism = Synthetic construct
SEQUENCE: 34
ccagctgtca acccgaataa                                        20

SEQ ID NO: 35           moltype = DNA  length = 22
```

```
FEATURE                  Location/Qualifiers
source                   1..22
                         mol_type = other DNA
                         organism = Synthetic construct
SEQUENCE: 35
gtcactggaa gccaggtaat ag                                            22

SEQ ID NO: 36            moltype = DNA  length = 22
FEATURE                  Location/Qualifiers
source                   1..22
                         mol_type = other DNA
                         organism = Synthetic construct
SEQUENCE: 36
cgattcactc gtactcttct gg                                            22

SEQ ID NO: 37            moltype = DNA  length = 20
FEATURE                  Location/Qualifiers
source                   1..20
                         mol_type = other DNA
                         organism = Synthetic construct
SEQUENCE: 37
ggcgatgggt gtctgataat                                               20

SEQ ID NO: 38            moltype = DNA  length = 22
FEATURE                  Location/Qualifiers
source                   1..22
                         mol_type = other DNA
                         organism = Synthetic construct
SEQUENCE: 38
tgtcaggttc atgtacgaaa gg                                            22

SEQ ID NO: 39            moltype = DNA  length = 21
FEATURE                  Location/Qualifiers
source                   1..21
                         mol_type = other DNA
                         organism = Synthetic construct
SEQUENCE: 39
agggtcgcga aatcaactat g                                             21

SEQ ID NO: 40            moltype = DNA  length = 22
FEATURE                  Location/Qualifiers
source                   1..22
                         mol_type = other DNA
                         organism = Synthetic construct
SEQUENCE: 40
gacccgtaat cccaactcta tg                                            22

SEQ ID NO: 41            moltype = DNA  length = 22
FEATURE                  Location/Qualifiers
source                   1..22
                         mol_type = other DNA
                         organism = Synthetic construct
SEQUENCE: 41
gagagccttc agctggttat ac                                            22

SEQ ID NO: 42            moltype = DNA  length = 22
FEATURE                  Location/Qualifiers
source                   1..22
                         mol_type = other DNA
                         organism = Synthetic construct
SEQUENCE: 42
ggcggacatg aatgacttta ac                                            22

SEQ ID NO: 43            moltype = DNA  length = 21
FEATURE                  Location/Qualifiers
source                   1..21
                         mol_type = other DNA
                         organism = Synthetic construct
SEQUENCE: 43
gcgacatctt tgacgctact a                                             21

SEQ ID NO: 44            moltype = DNA  length = 23
FEATURE                  Location/Qualifiers
source                   1..23
                         mol_type = other DNA
                         organism = Synthetic construct
SEQUENCE: 44
agtgagactg tcggaaacat tag                                           23
```

```
SEQ ID NO: 45          moltype = DNA  length = 2407
FEATURE                Location/Qualifiers
source                 1..2407
                       mol_type = other DNA
                       organism = Rotavirus A
SEQUENCE: 45
accgagctcg aattcatggc ttcgcttata tacaggcaac tgctcagcaa ttcgtatacc  60
gttgatctgt ctgacgagat tcaaattatc ggctcggaga agacacaaaa cgtcaccata  120
aacccgggac cgtttgcgca gacaggttat gcacctgtca attggggacc gggtgagaca  180
aacgactcaa caactgtcga gccagtcttg gacggcccgt atcaaccgac gacctttaat  240
ccaccggttt cgtattggat tcttctttcg cctagtaatg ccggtgtagt cgtcgaaggc  300
actaataact cagaccgttg gctcgcaact atattgatag aaccgaacgt aatttccgaa  360
agtcgcacat acacattgtt tggcagacag gagcaaatta cggtggaaaa tgtatcaaca  420
accaagtgga aattcgtcga ccttgccaaa accgatatca atggaacgtt cacgcagcat  480
ggtccgcttt tgtcggacac caaattgtac ggagtaatga aatttagtgg tcgtctgtac  540
acttataatg gagaaacacc caatgctacc acaggatatt atactaccac caattatgac  600
accgtgaaca tgaccagcta ttgtgacttc tatatcatac cgcgctctga agagtcagct  660
tgtactagtt atattaataa tggcctgccc ccaattcaga atacgcgtaa tgttgttcca  720
gtgagtttga cgtctcgctc catagtccat actagggcgc aagcaaatga agatattgtg  780
gtcagcaaaa catctctgtg gaaagagatg caatacaata gggatataac gatacgtttc  840
aaatttgcga acgctataat aaaaagcggt ggactgggtt acaagtggag cgagatttct  900
ttcaagccgg ccaactatca gtacaattat acgagagacg gtgaggtcat cactgcccat  960
actacctgta gtgtcaatgg tattaatgat tttagttaca atggaggctc cttgccgacc  1020
gattttgtga tcagcaggta tgaagtaata aaagaaaata gttatgtgta tgtggactat  1080
tgggatgact cacaggcttt cagaaacatg gtctatgtcc gtagtttggc tgccaatctc  1140
aattctgtta catgcacagg tggcaattat gattttagac tgcccgtggg tgcctggcct  1200
gttatgactg gaggcgctgt ctcactgcgt ccggccggcg ttacgctctc cacgcagttt  1260
acggattttg taagcttgaa ctctttgaga tttaggttca gcttgtcggt ggaagagcct  1320
ccttttacaa ttacacgcac tagggtgtcc ggactgtatg gtctcccggc ggcaaatcct  1380
aacaacggaa aggattacta cgagatactt ggtcgcttta gcctcatcag cctcgtgccg  1440
agcaacgacg attatcagac gcctatcatg aactctgtga ccgtgcgtca agaccttgaa  1500
cgccagctta acgaattgcg ccaagaattt aattcattga gtcaagaagt tgctatgagc  1560
cagcttatcg accttgcgct gcttcctctc gatatgttct ctatgttcag cggtataaag  1620
tcgaccatcg acgccgccaa atctatggcc acttcagtta tgaagaagtt taaacgttcg  1680
aacctcgcat cttctattag caccctcaca gattctctct cagacgctgc atccagtatt  1740
tcgaggaatc cgagtataag aagtgctgga tcttctgtgt cggtttggac agatataagt  1800
acccaagcga cagatatcag cgatactttc agaagtgtgt caacccagac gtcaacaatt  1860
tcgcgcaggc tccgtctgaa ggagataacg actcaaactg aaggcatgaa ttttgacgat  1920
atttcagccg ctgtgcttaa gacaaaaatc gataagtccg tgcaaatttc gcccaatacg  1980
ttgccggaca ttgttacgga ggcttccgag aaatttattc cgaatcgcac gtatcgtgtc  2040
attaaagacg atgaggtcct tgaggctgga accgacggcc gcttctttgc atacaaggtc  2100
gacactttcg atgaaatacc attcgacgtc caaaagttcg ccgaccttgt tactgacagc  2160
cctgtgataa gcgcgatcat tgactttaag acgcttaaaa atcttaacga caactacggt  2220
ataactaggg aacaggcttt caacctgctg cgttccgatc ctcgcgtctt gcgtgagttt  2280
attaatcagg agaacccaat tattcgcaac cgcatcgagc agctcattct ccagtgcagg  2340
cttaagggcg aaaacttgta ctttcaaggc catcaccatc accatcacta ggcggccgct  2400
taattaa                                                           2407

SEQ ID NO: 46          moltype = AA  length = 2373
FEATURE                Location/Qualifiers
source                 1..2373
                       mol_type = protein
                       organism = Rotavirus A
SEQUENCE: 46
METALASERL EUILETYRAR GGLNLEULEU SERASNSERT YRTHRVALAS PLEUSERASP  60
GLUILEGLNI LEILEGLYSE RGLULYSTHR GLNASNVALT HRILEASNPR OGLYPROPHE  120
ALAGLNTHRG LYTYRALAPR OVALASNTRP GLYPROGLYG LUTHRASNAS PSERTHRTHR  180
VALGLUPROV ALLEUASPGL YPROTYRGLN PROTHRTHRP HEASNPROPR OVALSERTYR  240
TRPILELEUL EUSERPROSE RASNALAGLY VALVALVALG LUGLYTHRAS NASNSERASP  300
ARGTRPLEUA LATHRILELE UILEGLUPRO ASNVALILES ERGLUSERAR GTHRTYRTHR  360
LEUPHEGLYA RGGLNGLUGL NILETHRVAL GLUASNVALS ERTHRTHRLY STRPLYSPHE  420
VALASPLEUA LALYSTHRAS PILEASNGLY THRPHETHRG LNHISGLYPR OLEULEUSER  480
ASPTHRLYSL EUTYRGLYVA LMETLYSPHE SERGLYARGL EUTYRTHRTY RASNGLYGLU  540
THRPROASNA LATHRTHRGL YTYRTYRTHR THRTHRASNT YRASPTHRVA LASNMETTHR  600
SERTYRCYSA SPPHETYRIL EILEPROARG SERGLUGLUS ERALACYSTH RSERTYRILE  660
ASNASNGLYL EUPROPROIL EGLNASNTHR ARGASNVALV ALPROVALSE RLEUTHRSER  720
ARGSERILEV ALHISTHRAR GALAGLNALA ASNGLUASPI LEVALVALSE RLYSTHRSER  780
LEUTRPLYSG LUMETGLNTY RASNARGASP ILETHRILEA RGPHELYSPH EALAASNALA  840
ILEILELYSS ERGLYGLYLE UGLYTYRLYS TRPSERGLUI LESERPHELY SPROALAASN  900
TYRGLNTYRA SNTYRTHRAR GASPGLYGLU VALILETHRA LAHISTHRTH RCYSSERVAL  960
ASNGLYILEA SNASPPHESE RTYRASNGLY GLYSERLEUP ROTHRASPPH EVALILESER  1020
ARGTYRGLUV ALILELYSGL UASNSERTYR VALTYRVALA SPTYRTRPAS PASPSERGLN  1080
ALAPHEARGA SNMETVALTY RVALARGSER LEUALAALAA SNLEUASNSE RVALTHRCYS  1140
THRGLYGLYA SNTYRASPPH EARGLEUPRO VALGLYALAT RPPROVALME TTHRGLYGLY  1200
ALAVALSERL EUARGPROAL AGLYVALTHR LEUSERTHRG LNPHETHRAS PPHEVALSER  1260
LEUASNSERL EUARGPHEAR GPHESERLEU SERVALGLUG LUPROPROPH ETHRILETHR  1320
ARGTHRARGV ALSERGLYLE UTYRGLYLEU PROALAALAA SNPROASNAS NGLYLYSASP  1380
TYRTYRGLUI LELEUGLYAR GPHESERLEU ILESERLEUV ALPROSERAS NASPASPTYR  1440
GLNTHRPROI LEMETASNSE RVALTHRVAL ARGGLNASPL EUGLUARGGL NLEUASNGLU  1500
```

-continued

```
LEUARGGLNG LUPHEASNSE RLEUSERGLN GLUVALALAM ETSERGLNLE UILEASPLEU  1560
ALALEULEUP ROLEUASPME TPHESERMET PHESERGLYI LELYSSERTH RILEASPALA  1620
ALALYSSERM ETALATHRSE RVALMETLYS LYSPHELYSA RGSERASNLE UALASERSER  1680
ILESERTHRL EUTHRASPSE RLEUSERASP ALAALASERS ERILESERAR GASNPROSER  1740
ILEARGSERA LAGLYSERSE RVALSERVAL TRPTHRASPI LESERTHRGL NALATHRASP  1800
ILESERASPT HRPHEARGSE RVALSERTHR GLNTHRSERT HRILESERAR GARGLEUARG  1860
LEULYSGLUI LETHRTHRGL NTHRGLUGLY METASNPHEA SPASPILESE RALAALAVAL  1920
LEULYSTHRL YSILEASPLY SSERVALGLN ILESERPROA SNTHRLEUPR OASPILEVAL  1980
THRGLUALAS ERGLULYSPH EILEPROASN ARGTHRTYRA RGVALILELY SASPASPGLU  2040
VALLEUGLUA LAGLYTHRAS PGLYARGPHE PHEALATYRL YSVALASPTH RPHEASPGLU  2100
ILEPROPHEA SPVALGLNLY SPHEALAASP LEUVALTHRA SPSERPROVA LILESERALA  2160
ILEILEASPP HELYSTHRLE ULYSASNLEU ASNASPASNT YRGLYILETH RARGGLUGLN  2220
ALAPHEASNL EULEUARGSE RASPPROARG VALLEUARGG LUPHEILEAS NGLNGLUASN  2280
PROILEILEA RGASNARGIL EGLUGLNLEU ILELEUGLNC YSARGLEULY SGLYGLUASN  2340
LEUTYRPHEG LNGLYHISHI SHISHISHIS HIS                              2373

SEQ ID NO: 47          moltype = DNA  length = 21
FEATURE                Location/Qualifiers
source                 1..21
                       mol_type = other DNA
                       organism = Synthetic construct
SEQUENCE: 47
gagccaacgg tctgagttat t                                           21

SEQ ID NO: 48          moltype = DNA  length = 21
FEATURE                Location/Qualifiers
source                 1..21
                       mol_type = other DNA
                       organism = Synthetic construct
SEQUENCE: 48
tcaaccgacg acctttaatc c                                           21

SEQ ID NO: 49          moltype = DNA  length = 21
FEATURE                Location/Qualifiers
source                 1..21
                       mol_type = other DNA
                       organism = Synthetic construct
SEQUENCE: 49
aatctcgctc cacttgtaac c                                           21

SEQ ID NO: 50          moltype = DNA  length = 18
FEATURE                Location/Qualifiers
source                 1..18
                       mol_type = other DNA
                       organism = Synthetic construct
SEQUENCE: 50
tagggcgcaa gcaaatga                                               18

SEQ ID NO: 51          moltype = DNA  length = 24
FEATURE                Location/Qualifiers
source                 1..24
                       mol_type = other DNA
                       organism = Synthetic construct
SEQUENCE: 51
cgactttata ccgctgaaca taga                                        24

SEQ ID NO: 52          moltype = DNA  length = 19
FEATURE                Location/Qualifiers
source                 1..19
                       mol_type = other DNA
                       organism = Synthetic construct
SEQUENCE: 52
gccgagcaac gacgattat                                              19
```